United States Patent [19]

Bova

[11] Patent Number: 6,129,930

[45] Date of Patent: *Oct. 10, 2000

[54] METHODS AND SUSTAINED RELEASE NICOTINIC ACID COMPOSITIONS FOR TREATING HYPERLIPIDEMIA AT NIGHT

[76] Inventor: David J. Bova, 11199 Sea Grass Cir., Boca Raton, Fla. 33498

[ * ] Notice: This patent is subject to a terminal disclaimer.

[21] Appl. No.: 08/814,974

[22] Filed: Mar. 6, 1997

Related U.S. Application Data

[63] Continuation-in-part of application No. 08/368,378, Jan. 14, 1995, which is a continuation-in-part of application No. 08/124,392, Sep. 20, 1993, abandoned.

[51] Int. Cl.⁷ .................................................. A61K 9/22
[52] U.S. Cl. ......................... 424/468; 424/464; 424/480
[58] Field of Search .................................. 424/464, 468, 424/480

[56] References Cited

U.S. PATENT DOCUMENTS

| | | |
|---|---|---|
| Re. 29,652 | 5/1978 | Fields et al. . |
| Re. 32,581 | 1/1988 | Scherm et al. . |
| 2,510,164 | 6/1950 | Woodward et al. . |
| 2,540,979 | 2/1951 | Clymer et al. . |
| 2,749,274 | 6/1956 | Buckwalter . |
| 2,798,837 | 7/1957 | Sahyun . |
| 2,798,838 | 7/1957 | Robinson . |
| 2,805,977 | 9/1957 | Robinson . |
| 2,851,453 | 9/1958 | Kennon et al. . |
| 2,857,313 | 10/1958 | Cooper et al. . |
| 3,065,143 | 11/1962 | Christenson et al. . |
| 3,424,842 | 1/1969 | Nurnberg . |
| 3,495,011 | 2/1970 | Fossel . |
| 3,590,117 | 6/1971 | Christenson et al. . |
| 3,626,071 | 12/1971 | Kariya et al. . |
| 3,629,393 | 12/1971 | Nakamota et al. . |
| 3,634,584 | 1/1972 | Poole . |
| 3,639,636 | 2/1972 | Barnhart . |
| 3,709,991 | 1/1973 | Miller . |
| 3,721,735 | 3/1973 | Thiffault . |
| 3,773,920 | 11/1973 | Nakamoto et al. . |
| 3,795,691 | 3/1974 | Douglas et al. . |
| 3,806,601 | 4/1974 | Mikite et al. . |
| 3,849,554 | 11/1974 | Winitiz . |
| 3,859,437 | 1/1975 | Weigand . |
| 3,862,332 | 1/1975 | Barnhart et al. . |
| 3,864,416 | 2/1975 | Albright et al. . |
| 3,870,790 | 3/1975 | Lowey et al. . |
| 3,923,972 | 12/1975 | Fields et al. . |
| 3,924,001 | 12/1975 | Albright et al. . |
| 3,930,017 | 12/1975 | Kummer et al. . |
| 3,951,821 | 4/1976 | Davidson . |
| 3,957,976 | 5/1976 | Sugimoto . |
| 3,959,492 | 5/1976 | Coulston . |
| 3,965,255 | 6/1976 | Bloch et al. . |
| 3,977,404 | 8/1976 | Theeuwes . |
| 3,987,160 | 10/1976 | Broughton et al. . |
| 3,992,536 | 11/1976 | Kleemann . |
| 4,002,641 | 1/1977 | Moller et al. . |
| 4,008,719 | 2/1977 | Theeuwes . |
| 4,011,339 | 3/1977 | Theeuwes et al. . |
| 4,014,334 | 3/1977 | Theeuwes et al. . |
| 4,014,987 | 3/1977 | Heller et al. . |
| 4,034,087 | 7/1977 | Voorhees . |
| 4,034,758 | 7/1977 | Theeuwes . |
| 4,058,122 | 11/1977 | Theeuwes et al. . |
| 4,067,876 | 1/1978 | Ferruti et al. . |
| 4,077,407 | 3/1978 | Theeuwes et al. . |
| 4,102,806 | 7/1978 | Kondo et al. . |
| 4,115,550 | 9/1978 | Fields et al. . |
| 4,116,241 | 9/1978 | Theeuwes et al. . |
| 4,117,111 | 9/1978 | Fields et al. . |
| 4,126,672 | 11/1978 | Sheth et al. . |
| 4,140,755 | 2/1979 | Sheth et al. . |
| 4,160,020 | 7/1979 | Ayers et al. . |
| 4,160,452 | 7/1979 | Theeuwes . |
| 4,166,902 | 9/1979 | Ferruti et al. . |
| 4,167,558 | 9/1979 | Sheth et al. . |
| 4,169,944 | 10/1979 | Scallen et al. . |
| 4,178,387 | 12/1979 | Diamond et al. . |
| 4,180,064 | 12/1979 | Heller et al. . |
| 4,182,902 | 1/1980 | Thiele et al. . |
| 4,203,439 | 5/1980 | Theeuwes . |
| 4,205,085 | 5/1980 | Shepherd . |
| 4,211,783 | 7/1980 | Shepherd . |
| 4,226,849 | 10/1980 | Schor . |
| 4,230,878 | 10/1980 | Shepherd . |
| 4,237,118 | 12/1980 | Howard . |
| 4,248,857 | 2/1981 | DeNeale et al. . |
| 4,251,519 | 2/1981 | Robbins et al. . |
| 4,255,449 | 3/1981 | Cavazza . |
| 4,256,108 | 3/1981 | Theeuwes . |
| 4,259,314 | 3/1981 | Lowey . |
| 4,261,970 | 4/1981 | Ogawa et al. . |
| 4,268,524 | 5/1981 | Cavazza . |
| 4,272,548 | 6/1981 | Gatzen et al. . |
| 4,279,898 | 7/1981 | Engel et al. . |
| 4,282,233 | 8/1981 | Vilani . |
| 4,283,382 | 8/1981 | Frank et al. . |
| 4,285,951 | 8/1981 | Hoefle . |
| 4,291,030 | 9/1981 | Mulinos . |

(List continued on next page.)

OTHER PUBLICATIONS

Remington's Pharmaceutical Sciences, pp. 1636–1637, 1990.
Urberg M et al: *Metabolism,* 36(9):896–899 (Sep., 1987).
Blankenhorn D H et al: *JAMA,* 257(23):159–166 (Jun. 19, 1987).

(List continued on next page.)

*Primary Examiner*—Jyothsna Venkat

[57] ABSTRACT

An orally administered antihyperlipidemia composition according to the present invention includes from about 250 to about 3000 parts by weight of nicotinic acid, and from about 5 to about 50 parts by weight of hydroxypropyl methylcellulose. Also, a method of treating hyperlipidemia in a hyperlipidemic having a substantially periodic physiological loss of consciousness, includes the steps of forming a composition having an effective antihyperlipidemic amount of nicotinic acid and a time release sustaining amount of a swelling agent. The method also includes the step of orally administering the composition to the hyperlipidemic once per day "nocturnally," that is in the evening or at night.

148 Claims, No Drawings

U.S. PATENT DOCUMENTS

| | | |
|---|---|---|
| 4,305,959 | 12/1981 | Shepherd . |
| 4,308,251 | 12/1981 | Dunn et al. . |
| 4,309,404 | 1/1982 | DeNeale et al. . |
| 4,310,545 | 1/1982 | Shepherd . |
| 4,318,914 | 3/1982 | Shepherd . |
| 4,326,525 | 4/1982 | Swanson et al. . |
| 4,348,399 | 9/1982 | Shepherd . |
| 4,353,887 | 10/1982 | Hess et al. . |
| 4,357,469 | 11/1982 | Schor . |
| 4,361,546 | 11/1982 | Stricker et al. . |
| 4,362,711 | 12/1982 | Cerami . |
| 4,367,217 | 1/1983 | Gruber et al. . |
| 4,369,172 | 1/1983 | Schor et al. . |
| 4,375,468 | 3/1983 | Dunn . |
| 4,382,143 | 5/1983 | Shepherd . |
| 4,389,393 | 6/1983 | Schor et al. . |
| 4,428,951 | 1/1984 | Hata et al. . |
| 4,440,940 | 4/1984 | Shepherd . |
| 4,452,775 | 6/1984 | Kent . |
| 4,454,108 | 6/1984 | Iida et al. . |
| 4,455,298 | 6/1984 | McFarlane et al. . |
| 4,457,907 | 7/1984 | Porter . |
| 4,461,759 | 7/1984 | Dunn . |
| 4,465,660 | 8/1984 | David et al. . |
| 4,472,436 | 9/1984 | Hooper . |
| 4,478,819 | 10/1984 | Hercelin et al. . |
| 4,485,105 | 11/1984 | Shepherd . |
| 4,522,804 | 6/1985 | Dunn . |
| 4,525,345 | 6/1985 | Dunn et al. . |
| 4,539,198 | 9/1985 | Powell et al. . |
| 4,540,566 | 9/1985 | Davis et al. . |
| 4,547,359 | 10/1985 | Zierenberg et al. . |
| 4,556,678 | 12/1985 | Hsiao . |
| 4,568,547 | 2/1986 | Herschler . |
| 4,571,333 | 2/1986 | Hsiao et al. . |
| 4,576,604 | 3/1986 | Guittard et al. . |
| 4,603,142 | 7/1986 | Burger et al. . |
| 4,605,666 | 8/1986 | Schmidt et al. . |
| 4,610,870 | 9/1986 | Jain et al. . |
| 4,624,950 | 11/1986 | Sasaki et al. . |
| 4,657,757 | 4/1987 | Hanna et al. . |
| 4,673,405 | 6/1987 | Guittard et al. . |
| 4,678,516 | 7/1987 | Alderman et al. . |
| 4,680,323 | 7/1987 | Lowey . |
| 4,684,516 | 8/1987 | Bhutani . |
| 4,690,824 | 9/1987 | Powell et al. . |
| 4,692,337 | 9/1987 | Ukigaya et al. . |
| 4,695,467 | 9/1987 | Uemura et al. . |
| 4,695,591 | 9/1987 | Hanna et al. . |
| 4,695,910 | 9/1987 | Maruyama et al. . |
| 4,696,762 | 9/1987 | Sander et al. . |
| 4,704,285 | 11/1987 | Alderman . |
| 4,708,834 | 11/1987 | Cohen et al. . |
| 4,710,519 | 12/1987 | Finnan et al. . |
| 4,713,245 | 12/1987 | Ando et al. . |
| 4,729,895 | 3/1988 | Makino et al. . |
| 4,734,285 | 3/1988 | Alderman . |
| 4,744,907 | 5/1988 | Elger et al. . |
| 4,747,881 | 5/1988 | Shaw et al. . |
| 4,749,575 | 6/1988 | Rotman . |
| 4,752,479 | 6/1988 | Briggs et al. . |
| 4,753,801 | 6/1988 | Oren et al. . |
| 4,755,544 | 7/1988 | Makino et al. . |
| 4,756,911 | 7/1988 | Drost et al. . |
| 4,758,581 | 7/1988 | Scherm et al. . |
| 4,759,923 | 7/1988 | Buntin et al. . |
| 4,764,374 | 8/1988 | Grimberg . |
| 4,775,483 | 10/1988 | Mookerjea et al. . |
| 4,775,535 | 10/1988 | Lowey . |
| 4,777,042 | 10/1988 | Toda et al. . |
| 4,784,858 | 11/1988 | Ventouras . |
| 4,789,549 | 12/1988 | Khan et al. . |
| 4,792,452 | 12/1988 | Howard et al. . |
| 4,792,554 | 12/1988 | Elben et al. . |
| 4,794,115 | 12/1988 | Takahashi et al. . |
| 4,795,327 | 1/1989 | Gaylord et al. . |
| 4,795,642 | 1/1989 | Cohen et al. . |
| 4,795,644 | 1/1989 | Zentner . |
| 4,803,079 | 2/1989 | Hsiao et al. . |
| 4,803,081 | 2/1989 | Falk et al. . |
| 4,812,316 | 3/1989 | Rossi et al. . |
| 4,814,183 | 3/1989 | Zentner . |
| 4,814,354 | 3/1989 | Ghebre-Sellassie et al. . |
| 4,824,672 | 4/1989 | Day et al. . |
| 4,824,677 | 4/1989 | Shah et al. . |
| 4,828,836 | 5/1989 | Elger et al. . |
| 4,830,859 | 5/1989 | Finnan et al. . |
| 4,834,965 | 5/1989 | Martani et al. . |
| 4,834,985 | 5/1989 | Elger et al. . |
| 4,837,032 | 6/1989 | Ortega . |
| 4,839,177 | 6/1989 | Colombo et al. . |
| 4,842,863 | 6/1989 | Nichimura et al. . |
| 4,849,229 | 7/1989 | Gaylord et al. . |
| 4,851,232 | 7/1989 | Urquhart et al. . |
| 4,851,233 | 7/1989 | Khan et al. . |
| 4,855,143 | 8/1989 | Lowery . |
| 4,857,336 | 8/1989 | Khanna et al. . |
| 4,866,058 | 9/1989 | Izydore et al. . |
| 4,871,548 | 10/1989 | Edgren et al. . |
| 4,882,167 | 11/1989 | Jang . |
| 4,886,669 | 12/1989 | Ventouras . |
| 4,888,178 | 12/1989 | Rotini et al. . |
| 4,892,741 | 1/1990 | Ohm et al. . |
| 4,911,917 | 3/1990 | Kuhrts . |
| 4,915,952 | 4/1990 | Ayer et al. . |
| 4,920,115 | 4/1990 | Nestler et al. . |
| 4,920,123 | 4/1990 | Beyer, Jr. . |
| 4,925,905 | 5/1990 | Boeckh et al. . |
| 4,935,246 | 6/1990 | Ahrens . |
| 4,940,588 | 7/1990 | Sparks et al. . |
| 4,942,040 | 7/1990 | Ragnarsson et al. . |
| 4,946,870 | 8/1990 | Partain, III et al. . |
| 4,946,963 | 8/1990 | Izydore et al. . |
| 4,952,402 | 8/1990 | Sparks et al. . |
| 4,959,478 | 9/1990 | Moller et al. . |
| 4,963,367 | 10/1990 | Ecanow . |
| 4,965,252 | 10/1990 | Kuhrts . |
| 4,966,768 | 10/1990 | Michelucci et al. . |
| 4,968,508 | 11/1990 | Oren et al. . |
| 4,970,081 | 11/1990 | Frisbee . |
| 4,973,469 | 11/1990 | Mulligan et al. . |
| 4,983,398 | 1/1991 | Gaylord et al. . |
| 4,990,535 | 2/1991 | Cho et al. . |
| 4,992,278 | 2/1991 | Khanna . |
| 4,994,276 | 2/1991 | Baichwal et al. . |
| 4,996,058 | 2/1991 | Sinnreich . |
| 4,997,658 | 3/1991 | Alberts et al. . |
| 4,999,380 | 3/1991 | Berger et al. . |
| 5,009,895 | 4/1991 | Lui . |
| 5,015,479 | 5/1991 | Mulligan et al. . |
| 5,022,774 | 6/1991 | Kageyama et al. . |
| 5,023,245 | 6/1991 | Kuhrts . |
| 5,025,012 | 6/1991 | Miura et al. . |
| 5,032,406 | 7/1991 | Dansereau et al. . |
| 5,034,528 | 7/1991 | Izydore et al. . |
| 5,039,341 | 8/1991 | Meyer . |
| 5,047,248 | 9/1991 | Calanchi et al. . |
| 5,096,714 | 3/1992 | Kuhrts et al. . |
| 5,100,675 | 3/1992 | Cho et al. . |
| 5,110,817 | 5/1992 | Beyer, Jr. . |
| 5,126,145 | 6/1992 | Evenstad et al. . |
| 5,128,142 | 7/1992 | Mulligan et al. . |

| | | |
|---|---|---|
| 5,130,333 | 7/1992 | Pan et al. . |
| 5,132,116 | 7/1992 | Sournac et al. . |
| 5,133,974 | 7/1992 | Paradissis et al. . |
| 5,145,678 | 9/1992 | Gakic et al. . |
| 5,167,964 | 12/1992 | Muhammad et al. . |
| 5,169,638 | 12/1992 | Dennis et al. . |
| 5,169,639 | 12/1992 | Baichwal et al. . |
| 5,169,640 | 12/1992 | France et al. . |
| 5,171,570 | 12/1992 | Takemori et al. . |
| 5,178,854 | 1/1993 | Asami et al. . |
| 5,182,298 | 1/1993 | Helms et al. . |
| 5,188,839 | 2/1993 | Pearmain . |
| 5,190,940 | 3/1993 | Commons et al. . |
| 5,190,970 | 3/1993 | Pan et al. . |
| 5,196,440 | 3/1993 | Bertolini et al. . |
| 5,211,958 | 5/1993 | Akkerboom et al. . |
| 5,213,808 | 5/1993 | Bar-Shalom et al. . |
| 5,256,689 | 10/1993 | Chiang . |
| 5,258,401 | 11/1993 | Berger et al. . |
| 5,260,305 | 11/1993 | Dennick . |
| 5,262,165 | 11/1993 | Govil et al. . |
| 5,262,435 | 11/1993 | Joshua et al. . |
| 5,264,226 | 11/1993 | Graille et al. . |
| 5,268,181 | 12/1993 | O'Neill et al. . |
| 5,278,067 | 1/1994 | Dawson et al. . |
| 5,286,736 | 2/1994 | Soyka et al. . |
| 5,314,697 | 5/1994 | Kwan et al. . |

OTHER PUBLICATIONS

Canner P L et al: *JACC*, 8(6):1245–1255 (Dec., 1986).
Sokoloski T D: *Solutions and Phase Equilibria*, in Remington's 17th Edition Pharmaceutical Sciences, Mack Publishing Company, 207–208 (1985).
Knopp R H et al: *Metabolism*, 34(7):642–650 (Jul. 1985).
Korsmeyer R W et al: *Journal of Pharmaceutical Sciences*, 72(10):1189,1191 Oct. 1983.
Dow Chemical Company publication, 1–15 (1985).
The Merck Index, Merck & Co. Inc., Tenth Edition, 809, 520,351,466 (1983).
Malkowska S et al: *Drug Development and Industrial Pharmacy*, Marcel Dekker, Inc., 9(3):349–361 (1983).
Blum C B et al: *JAMA*, 261(24):3582–3587 (1989).
1989 Dow Chemical Company publication which appears to relate to formulating for controlled release with Methocel premium cellulose ethers.
Kowalski R.E.: *The 8–Week Cholesterol Cure*, Harper & Row, Publishers, 95–115 and notes 345–346 (1989).
Manninen M et al: *JAMA*, 260(5):641–651 (1988).
Figge H L et al: *J. Clin. Pharmacol.*, 28:1136–1140 (1988).
Figge H L et al: *Pharmacotherapy*, 8(5):287–294 (1988).
Urberg M et al: *The Journal of Family Practice*, 27(6):603–606 (1988).
Wahlberg G et al: *Acta. Med. Scand.*, 224:319–327 (1988).
*Chain Drug Review Publication*, p. 12, Jun. 6, 1988, P. Leiner.
Cooper K H: *Bantam Books*, Dr. Kenneth H. Cooper's Preventive Medicine Program, Controlling Cholesterol, 244–253 (1988).
Laguna O et al: *Annales Pharmaceutiques Francaises*, 33(5):235–242 (1975).
Fleischman A I et al: *Fed. Proc.* 34(1), 248 (1975).
*Remington's Pharmaceutical Sciences*, 1576–1587 (1975).
*Remington's Pharmaceutical Sciences*, 1242–1251 (1975).
Schlierf G et al: *Nutr. Metabol.*, 13:80–91 (1971).
Barter P J et al: *The Journal of Clinical Investigation*, 50:583–591 (1971).

Miettinen T A: *Annals of Clinical Research*, 2:300–320 (1970).
Ekström–Jodal B et al: *Pharmacologia Clinica*, 2:86–89 (1970).
Lapidus H et al: *Journal of Pharmaceutical Sciences*, 57(8):1292–1301 (Aug. 1968).
Carlson L A et al: *Acta Med Scand*, 183(5):457–465 (May 1968).
Carlson L A et al: *J. Internal Medicine*, 226:271–76 (1989).
Rader J I et al: *The American Journal of Medicine*, 92:77–81 (Jan., 1992).
Etchason J A et al: *Mayo Clin. Proc.*, 66:23–28 (1991).
Keenan J M: *JAMA Specialty Journal Abstracts*, 266(16):2209 (1991).
Keenan J M et al: *Arch. Intern. Med.*, 151:1424–1432 (Jul. 1991).
Henkin Y et al: *JAMA*, 264(2):241–243 (1990).
Handbook of Nonprescription Drugs, Nutritional Supplements, 9th Edition, *American Pharmaceutical Association*, 470–471 (1990).
Schulman K A et al: *JAMA*, 264(23):3025–3033 (Dec. 19, 1990).
Brown G et al: *The New England Journal of Medicine*, 323(19):1289–1298 (Nov. 8, 1990).
Alderman J D et al: *Am. J. Cardiol.*, 64(12):725–729 (Oct. 1, 1989).
Alderman, JD et al: *Clinical Research: Ischemic Heart Disease—Drug Therapy*, Abstracts of the 58th Scientific Sessions, 1883, III–471 (1985).
Buriet P et al: *Pharm. ACTA Helv.*, 33(7–8):189–197 (1980).
Davis S S et al: *Modern Concepts in Nitrate Delivery Systems*, 29–37, edited by A.A.J. Goldberg and D.G. Parsons, 1983: Royal Society of Medicine International Congress and Symposium Series No. 54, published jointly by Academic Press Inc. (London) Ltd., and the Royal Society of Medicine.
Salomon J L et al: *Pharm. ACTA Helv.*, 54(3):82–85 (1979).
Ibrahim, S A et al: *Pharmazie*, 35(8):567 (1980).
Pintye–Hodi K et al: *Pharmazier*, 35(3):168–170 (1980).
Shepherd J et al: *J. Clin. Invest.*, 63:858–867 (May, 1979).
The Coronary Project Research Group: *JAMA*, 231(4):36–381 (Jan. 27, 1975).
Chowhan T et al: *Journal of Pharmaceutical Sciences*, 67(10):1385–1389 Oct. 1978).
Salomon J L et al: *Pharm. ACTA Helv.*, 54(3):75–85 (1979).
Salomon J L et al: *Pharm. Ind.*, 41(8):799–802 (1979).
Abumrad N A et al: *Journal of Lipid Research*, 19:423–432 (1978).
Japanese Patent Abstract, No. 0049312, which is dated Apr. 1980.
PCT Publication No. WO 84/00104, which was published on Jan. 19, 1984.
EPO Patent Abstract, No. 0109320, which is dated May 23, 1984.
EPO Patent Application No. 0126453, which is dated Nov. 28, 1984.
United Kingdom Patent Application No. 2 141 338 A, which was published on Dec. 19, 1984.
United Kingdom Patent Application No. 2 154 874 A, which was published on Sep. 18, 1985.
EPO Patent Publication No. 0 109320, which was published on Jun. 25, 1986.
Jacobson T A et al: *The American Journal of Cardiology*, 73:25D–29D (May 26, 1994).

Kane J P et al: *The New England Journal of Medicine*, 304(5):251–258 (Jan. 29, 1981).
Chowhan Z T et al: *Journal of Pharmaceutical Sciences*, 70(10):1134–1139 (Oct., 1981).
Cayen M N: *Drug Metabolism Reviews*, 11(2):291–323 (1980).
Rowland M et al: *Clinical Pharmacokinetics: Concepts and Applications* publication, Lea & Febiger, 111 (1980).
Chowhan Z T: *Journal of Pharmaceutical Sciences*, 69(1):1–3 (Jan., 1980).
Gudsoorkar, V R et al: *Indian Drugs & Pharmaceuticals Industry*, 3–4 (Jul.–Aug. 1980).
Krycer I et al: *Powder Technology*, 34:39–51 (1983).
1982 Dow Chemical Company publication is entitled "Technical Information: Methods of Formulating Controlled Release Products Outside the Forest Lab Patent U.S. 4,389,393 Claims."
1982 Dow Chemical Company publication is entitled "Formulating Sustained Release Pharmaceutical Products with Methocel."
1987 Dow Chemical Company publication is entitled "Formulating for Controlled Release with Methocel cellulose Ethers."
1988 Slow–Niacin® Advertisement, *American Druggist*, 141–142 (Apr., 1988.
Hunninghake D B: *Upsher–Smith Laboratories, Inc.* publication 1990.
1988 Regulatory Letter addressed to Upsher–Smith Laboratories, and dated Jun. 1988.
1989 Dow Chemical Company publication is entitled "Formulating for Controlled Release with Methocel cellulose Ethers".
Canadian Patent No. 603,690, which issued on Aug. 16, 1960 to Hamada.
French Patent No. 1.302.362, which issued on Jul. 23, 1962.
Japanese Patent Abstract, No. 40–2053, which is dated Feb. 1965.
Japanese Patent Abstract No. 46–18151, which is dated May 1971.
Lapidus H: *Chemistry*, 2363–B–2364–B (1967).
Dow Chemical: *Handbook on Methocel\* Cellulose Ether Products*, 1960.
Svedmyr N: *Clinical Pharmacology and Therapeutics*, 559–570 (1960.
Alderman J D et al: *Clinical Research*, Abstract 1883, III–471 (Oct. 1985).
Carlson, L A: *Annals New York Academy of Sciences*, 119–142 (1985).
Dow Chemical: (1985) appears to relate to product designation changes for methocel cellulose ethers.
Kassem A A et al: *Jami at Al–Qahira, Faculty of Pharmacy, Bulletin*, Cairo, 19(1):275–306 (1980).
Lapidus H: *Chemistry, Abstract*, (order No. 67–14, 728) 2363–B–2364–B (1967).
Dow Chemical Company Publication: (1974) appears to relate to a handbook on methocel cellulose ether products.
Svedymr N et al: *Clinical Pharmacology and Therapeutics*, 10(4):559–570 (1974).
Reexamination Certificate No. B1 4,389,393 Published Oct. 22, 1985.
Mahl M: *The American Journal of the Medical Sciences*, 64:673–677 (Dec., 1963).
Carlson L A et al: *Acta Medica Scandinavica*, 172:641–645 (fasc. 6, 1962).
Carlson L A: *Acta Medica Scandinavica*, 173:719–722 (fasc. 6, 1963).
Berge K G et al: *American Journal of Medicine*, 31:24–35 (Jul. 1961).
Lapidus H et al: *Journal of Pharmaceutical Sciences*, 57(8):1292–1301 (Aug. 1968).
Christensen N A et al: *J.A.M.A.*, 177(8):76–80 (Aug. 26, 1961).
Carlson L A et al: *The Journal of Clinical Investigation*, 47:1795–1805 (1968).
Altschul R et al: *Academic Press Inc.*, 51:308–309 (1954).
Carlson L A: *Progr. Biochem. Pharmacol.*, 3:151–166 (1967).
Miller O N et al: *American Journal of Clinical Nutrition*, 8:480–490 (Jul.–Aug. 1960).
Pinter E.J. et al: *Preliminary Communications*, 27:440–443 (Mar. 1967).
Lapidus H: *University Microfilms International*, Thesis, Rutgers University, 1–117, 1983.
Carlson L A: *Annals New York Academy of Sciences*, III(471):118–143 (1960).
Lapidus H et al: *Journal of Pharmaceutical Sciences*, 55(8):840–843 (Aug. 1966).
Dow Chemical: (1960) appears to relate to product designation changes for methocel cellulose ethers.
Kassem A A et al: *Department of Pharmaceuticals, Faculty of Pharmacy, Cairo University*, 275–306 (1960).
Huber H E et al: *Journal of Pharmaceutical Sciences*, 55:974–976 (Sep. 1966).
Carlson L A: *Clinica Crimica Acta*, 13:349–350 (1966).
Carlson L A et al: *Acta Medica Scandinavica*, 179:453–461 (Apr. 1966).
Altschul R et al: *Charles C. Thomas*, 42–135 (1964).
Letter, *JAMA*, 264(2):181 (Jul. 11, 1990).
Schlierf G et al: *Artery*, 3(2):174–179 (1977).
Schlierf G et al: *J. Clin. Invest.*, 52(3):732–740 (Mar., 1973).
Abstract, Schlierf G et al: *Pharmacological Control of Lipid Metabolism, Proceedings of the Fourth International Symposium on Drugs Affecting Lipid Metabolism*, Philadelphia, PA, 26:319–320 (Sep., 1971).
Criscuoli M et al: *Artherosclerosis*, 53(1):59–68 (1984).
Renzetti A R et al: *J. Pharm Pharmacol.*, 37(12):906–909 (Dec. 1985).
Miettinen T A: *Annals of Clinical Research*, 12:295–298 (1980).
Miettinen T A: *Metabolism*, 34(5):425–430 (May, 1985.
Miettinen T A: *J. Lipid Research*, 23:466–473 (1982).
Regulatory Letter, Department of Health & Human Services, addressed to Nutritional Products, Inc. (Feb. 21, 1989).
Luria M H: *Arch. Intern. Med.*, 148:2493–2495 (1988).
Kruse W et al: *Eur. J. Clin. Pharmacol.*, 16:11–15 (1979).
Altschul R: *Arch. Biochem. Bophys*, 54:448–559 (1955).
Carlson L A et al: *Acta Med. Scand.*, 183:457–465 (1968).
Neuvonen P J et al: *Br. J. Clin. Pharmac.*, 32:473–476 (1991).
Keenan J M et al: *JAGS*, 40:12–18 (1992).
Cayen M N et al: *Artherosclerosis*, 45(3):281–290 (Dec., 1982).
Subissi A et al: *J. Pharm. Pharmacol.*, 35(9):571–575 (Sep. 1983).

METHODS AND SUSTAINED RELEASE NICOTINIC ACID COMPOSITIONS FOR TREATING HYPERLIPIDEMIA AT NIGHT

RELATED PATENT APPLICATIONS

This application for U.S. patent is a U.S.C., Title 35, §111(a) application which is a continuation-in-part of U.S. patent application Ser. No. 08/368,378 filed Jan. 14, 1995, which is a continuation-in-part of U.S. patent application Ser. No. 08/124,392, filed Sep. 20, 1993 abandoned.

FIELD OF THE INVENTION

This invention generally relates to compositions of nicotinic acid useful for treating hyperlipidemia and methods of treating hyperlipidemia employing such compositions. More particularly, the present invention employs a composition of nicotinic acid, derivatives and mixtures thereof, and a swelling agent to form a time release sustaining composition for nocturnal or evening dosing. Specifically, the present invention employs a composition of nicotinic acid and hydroxypropyl methylcellulose to treat hyperlipidemia in a once per day oral dosage form given during the evening hours.

BACKGROUND

Nicotinic acid has been used for many years in the treatment of hyperlipidemia. This compound has long been known to exhibit the beneficial effects of reducing total cholesterol, low density lipoproteins or "LDL cholesterol", triglycerides and apolipoprotein a (Lp(a)) in the human body, while increasing desirable high density lipoproteins or "HDL cholesterol".

Nicotinic acid has normally been administered three times per day after meals. This dosing regimen is known to provide a very beneficial effect on blood lipids as discussed in Knopp et al; "Contrasting Effects of Unmodified and Time-Release Forms of Niacin on Lipoproteins in Hyperlipidernic Subjects: Clues to Mechanism of Action of Niacin"; Metabolism 34/7, 1985, page 647. The chief advantage of this profile is the ability of nicotinic acid to decrease total cholesterol, LDL cholesterol, triglycerides and Lp(a) while increasing HDL particles. While such a regimen does produce beneficial effects, cutaneous flushing and the like still often occurs in the hyperlipidemics to whom the compound is administered.

In order to avoid or reduce the cutaneous flushing, a number of materials have been suggested for administration with an effective antihyperlipidemic amount of nicotinic acid, including guar gum in U.S. Pat. No. 4,965,252, and mineral salts as disclosed in U.S. Pat. No. 5,023,245; or inorganic magnesium salts as reported in U.S. Pat. No. 4,911,917. These materials have been reported to avoid or reduce the cutaneous flushing side effect commonly associated with nicotinic acid treatment.

Another method of avoiding or reducing the side effects associated with immediate release niacin is the use of sustained release formulations. Sustained release formulations are designed to slowly release the compound from the tablet or capsule. The slow drug release reduces and prolongs blood levels of drug and thus minimizes the side effects. Sustained release formulations of niacin have been developed, such as Nicobid™ capsules (Rhone-Poulenc Rorer), Endur-acin™ (Innovite Corporation) and U.S. Pat. No. 5,126,145 which describes a sustained release niacin formulation containing two different types of hydroxypropyl methylcellulose and a hydrophobic component.

Studies in hyperlipidemic patients have been conducted with a number of sustained release niacin products. These studies have demonstrated that the sustained release products do not have the same advantageous lipid altering effects as immediate release niacin, and in fact often have a worse side effect profile compared to the immediate release product. The major disadvantage of the sustained release formulations, as can be seen in Knopp et al., 1985, is the significantly lower reduction in triglycerides (−2% for the sustained release versus −38% for the immediate release) and lower increase in HDL cholesterol, represented as $HDL_2$ particles which are known by the art to be most beneficial, (−5% for the sustained release versus +37% for the immediate release).

Additionally, sustained release niacin formulations have been noted as causing greater incidences of liver toxicity as described in Henken et al (Am J Med 91:1991 1991) and Dalton et al (Am J Med 93: 102 1992). There is also great concern regarding the potential of these formulations in disrupting glucose metabolism and uric acid levels.

In a recent edition of the JOURNAL OF THE AMERICAN MEDICAL ASSOCIATION (JAMA), an article appeared which presented research results investigating the liver toxicity problems associated with a sustained release form of nicotinic acid. "A Comparison of the Efficacy and Toxic Effects of Sustained- vs. Immediate-Release Niacin in Hypercholesterolemic Patients", McKenney et al., JAMA, Vol. 271, No. 9, Mar. 2, 1994, page 672. The article presented a study of twenty-three patients. Of that number, 18 or 78 percent were forced to withdraw because liver function tests (LFTs) increased indicating potential liver damage. The conclusion of the authors of that article was that the sustained release form of niacin "should be restricted from use."

A similar conclusion was reached in an article authored by representatives of the Food and Drug Administration and entitled "Hepatic Toxicity of Unmodified and Time-Release Preparations of Niacin", Rader, et al., THE AMERICAN JOURNAL OF MEDICINE, Vol. 92, January 1992, page 77. Because of these studies and similar conclusions drawn by other health care professionals, the sustained release forms of niacin have experienced limited utilization.

Therefore, it can be seen from the scientific literature that there is a need for development of a sustained release niacin formulation and a method of delivering said formulation which would provide hyperlipidemic patients with "balanced lipid alteration", i.e. reductions in total cholesterol, LDL cholesterol, triglycerides and Lp(a) as well as increases in HDL particles, with an acceptable safety profile, especially as regards liver toxicity and effects on glucose metabolism and uric acid levels.

SUMMARY OF THE INVENTION

In brief, the present invention alleviates and overcomes certain of the above-identified problems and shortcomings of the present state of nicotinic acid therapy through the discovery of novel nicotinic acid formulations and methods of treatment.

It is therefore, an object of the present invention to provide a composition of nicotinic acid or any compound which is metabolized by the body to form nicotinic acid for treating hyperlipidemia.

It is another object of the present invention to provide a composition as above, which has a time release sustaining characteristic.

It is yet another object of the present invention to provide a method for employing a composition as above, for treating hyperlipidemia, which results in little or no liver damage.

At least one or more of the foregoing objects, together with the advantages thereof over the known art relating to the treatment of hyperlipidemia, which shall become apparent from the specification which follows, are accomplished by the invention as hereinafter described and claimed.

In general the present invention provides an improved antihyperlipidemia composition of the oral type employing an effective antihyperlipidemic amount of nicotinic acid, wherein the improvement comprises compounding the nicotinic acid with from about 5% to about 50% parts by weight of hydroxypropyl methylcellulose per hundred parts by weight of tablet or formulation.

The present invention also provides an orally administered antihyperlipidemia composition which comprises from about 30% to about 90% parts by weight of nicotinic acid; and, from about 5% to about 50% parts by weight of hydroxypropyl methylcellulose.

The present invention also includes a method of treating hyperlipidemia in a hyperlipidemic. The method comprises the steps of forming a composition which comprises an effective antihyperlipidemic amount of nicotinic acid and an amount of excipients to provide sustained release of drug. The method also includes the step of orally administering the composition to the hyperlipidemic nocturnally.

A method of treating hyperlipidemia in a hyperlipidemic according to the invention, comprises dosing the hyperlipidemic with an effective antihyperlipidemic amount of nicotinic acid or compound metabolized to nicotinic acid by the body. The dose is given once per day in the evening or at night, combined with a pharmaceutically acceptable carrier to produce a significant reduction in total and LDL cholesterol as well as a significant reduction in triglycerides and Lp(a), with a significant increase in HDL cholesterol.

The above features and advantages of the present invention will be better understood with reference to the following detailed description and examples. It should also be understood that the particular methods and formulations illustrating the present invention are exemplary only and not to be regarded as limitations of the present invention.

DETAILED DESCRIPTION OF THE INVENTION

By way of illustrating and providing a more complete appreciation of the present invention and many of the attendant advantages thereof, the following detailed description and examples are given concerning the novel methods and formulations.

The present invention employs nicotinic acid or a compound other than nicotinic acid itself which the body metabolizes into nicotinic acid, thus producing the same effect as described herein. The other compounds specifically include, but are not limited to the following: nicotinyl alcohol tartrate, d-glucitol hexanicotinate, aluminum nicotinate, niceritrol and d, 1-alpha-tocopheryl nicotinate. Each such compound will be collectively referred to hereinbelow by "nicotinic acid."

As stated hereinabove, nicotinic acid has been employed in the past for the treatment of hyperlipidemia, which condition is characterized by the presence of excess fats such as cholesterol and triglycerides, in the blood stream. According to the present invention, a sustained release composition of nicotinic acid is prepared as an example. By "sustained release" it is understood to mean a composition which when orally administered to a patient to be treated, the active ingredient will be released for absorption into the blood stream over a period of time. For example, it is preferred that in a dosage of about 1500 milligrams (hereinafter "mgs") of nicotinic acid, approximately 100 percent of the nicotinic acid will be released to the blood stream in about 4 to about 24 hours.

The specific sustained release composition according to the present invention employs an effective antihyperlipidemic amount of nicotinic acid. By "effective antihyperlipidemic amount" it is understood to mean an amount which when orally administered to a patient to be treated, will have a beneficial effect upon the physiology of the patient, to include at least some lowering of total cholesterol, LDL cholesterol, triglycerides and Lp(a) and at least some increase in HDL cholesterol in the patient's blood stream. An exemplary effective antihyperlipidemic amount of nicotinic acid would be from about 250 mgs to about 3000 mgs of nicotinic acid to be administered according to the invention as will be more fully described hereinbelow. This amount will vary dependent upon a number of variables, including the psychological needs of the patient to be treated.

Preferably, there is also included in the sustained release composition according to the present invention, a swelling agent which is compounded with the nicotinic acid, such that when the composition is orally administered to the patient, the swelling agent will swell over time in the patient's gastrointestinal tract, and release the active nicotinic acid, or a compound which produces nicotinic acid into the gastrointestinal system for absorption into the blood stream, over a period of time. As is known in the art, such swelling agents and amounts thereof, may be preselected in order to control the time release of the active ingredient. Such swelling agents include, but are not limited to, polymers such as sodium carboxymethylcellulose and ethylcellulose and waxes such as bees wax and natural materials such as gums and gelatins or mixtures of any of the above. Because the amount of the swelling agent will vary depending upon the nature of the agent, the time release needs of the patient and the like, it is preferred to employ amounts of the agent which will accomplish the objects of the invention.

An exemplary and preferred swelling agent is hydroxypropyl methylcellulose, in an amount ranging from about 5% to about 50% parts by weight per 100 parts by weight of tablet or formulation. The preferred example will ensure a sustained time release over a period of approximately 4–24 hours as demonstrated by in vitro dissolution techniques known to the art.

A binder may also be employed in the present compositions. While any known binding material is useful in the present invention, it is preferred to employ a material such as one or more of a group of polymers having the repeating unit of 1-ethenyl-2-pyrrolidinone. These polymers generally have molecular weights of between about 10,000 and 700,000, and are also known as "povidone".

Amounts of the binder material will of course, vary depending upon the nature of the binder and the amount of other ingredients of the composition. An exemplary amount of povidone in the present compositions would be from about 1% to about 5% by weight of povidone per 100 parts by weight of the total formulation.

Processing aids such as lubricants, including stearic acid, may also be employed, as is known in the art. An exemplary amount of stearic acid in the present compositions would be from about 0.5% to about 2.0% by weight per 100 parts by weight of tablet or formulation.

Examples of various embodiments of the present invention will now be further illustrated with reference to the following examples.

General Experimental

In order to demonstrate the effectiveness of the compositions and method of the present invention over known antihyperlipidemia compositions and methods heretofore known in the art, a number of substantially identical composition were prepared according to the disclosure hereinabove. The composition ingredients and amounts are listed in TABLE IA hereinbelow.

TABLE IA

Test Tablet Composition

| Ingredient | 375 mg. | 500 mg | 750 mg |
|---|---|---|---|
| Nicotinic Acid | 375.0 | 500.0 | 750.0 |
| Hyroxypropyl methylcellulose | 188.7 | 203.0 | 204.7 |
| Povidone | 12.9 | 17.2 | 25.9 |
| Stearic Acid | 5.8 | 7.3 | 9.9 |
| TOTAL | 582.4 mg | 727.5 mg | 990.5 mg |

The ingredients were compounded together to form a tablet. More specifically, Niaspan® once-daily tablets in accordance with the present invention utilize a hydrophilic matrix controlled drug delivery system. This is a dynamic system composed of polymer wetting, polymer hydration and polymer disintegration-dissolution. The mechanism by which drug release is controlled depends on, for example, initial polymer wetting, expansion of the gel layer, tablet erosion and niacin solubility. After initial wetting, the hydrophilic polymer starts to partially hydrate, forming a gel layer. As water permeates into the tablet increasing the thickness of the gel layer, drug diffuses out of the gel layer. As the outer layer of the tablet becomes fully hydrated it erodes. It is believed that this erosion results in additional drug release. The controlled release from this matrix delivery system can be modified depending on the type and molecular weight of hydrophilic polymer used.

A Niaspan® formulation consists of Niacin, Methocel® E10M Premium, Povidone K90 and Hystrene 5016 (stearic acid). Methocel® E10M Premium is utilized as a controlled-release agent in the Niaspan® formulation. Methocel is a partly O-methylated and O-(2-hydroxypropylated) cellulose and is available in several grades which vary in terms of viscosity and degree of substitution. Methocel is manufactured by Dow Chemical.

Povidone K90 is employed as a granulating/binding agent in a Niaspan® formulation. Povidone is a synthetic polymer consisting of linear 1-vinyl-2-pyrrolidone groups, the degree of polymerization of which results in polymers of various molecular weights, or as indicated above. It is characterized by its viscosity in aqueous solution, relative to that of water, expressed as a K-value, ranging from 10–120. Povidone K90 has an approximate molecular weight of 1,000,000. Povidone is a hygroscopic, water soluble material. Povidone K90 present in a Niaspan® formulation is manufactured by ISP (International Specialty Products). Hystrene 5016 is utilized as an external lubricant in the Niaspan® formulation. Hystrene 5016 is a mixture of stearic acid and palmitic acid. The content of stearic acid is not less than about 40.0% and the sum of the two acids is not less than about 90.0%. Hystrene 5016 is manufactured by Witco. Refer to Table IB for Niaspan® formulation details.

Qualitatively, the four tablet strength formulations are identical. The major component of each formulation is a granulated mixture of Niacin, Methocel E10M and Povidone K90. The granulation process improves compression properties.

TABLE IB

Niaspan ® Tablet Formulations

| Niaspan ® Product | 375 mg Tablets | 500 mg Tablets | 750 mg Tablets | 1000 mg Tablets |
|---|---|---|---|---|
| Formulation, %/Tablet | | | | |
| Niacin | 64.4 | 70.5 | 77.4 | 83.1 |
| Methocel E10M Premium (Intragranular) | 7.4 | 8.1 | 8.9 | 9.5 |
| Povidone K90 | 2.2 | 2.4 | 2.7 | 2.9 |
| Methocel E10M Premium (Extragranular) | 25.0 | 18.0 | 10.0 | 3.5 |
| Hystrene 5016 (Stearic Acid) | 1.0 | 1.0 | 1.0 | 1.0 |
| Tablet weight, mg | 582.5 | 709.5 | 968.6 | 1203.6 |

Niaspan® formulations are presented in white caplet shape tablets. Caplet dimensions differ with respect to product strength. The 375 mg and 500 mg Niaspan® tablets are compressed with tooling measuring approximately 0.687" in length×0.281" by width. The length and width of the 750 mg and 1000 mg tooling measures approximately 0.750"×0.320". Target tablet weight and hardness dictate thickness across the four Niaspan® products. The production of the Niaspan® tablets will now be described generally as set forth below.

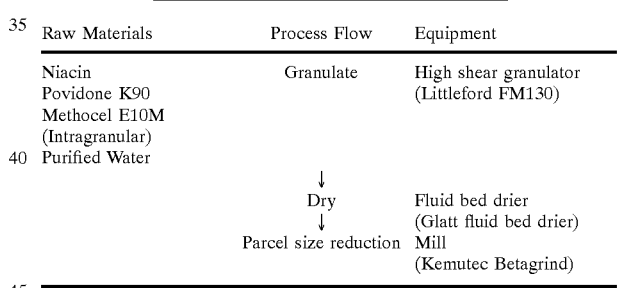

| Niaspan ® Granulation Process Flow Chart | | |
|---|---|---|
| Raw Materials | Process Flow | Equipment |
| Niacin<br>Povidone K90<br>Methocel E10M<br>(Intragranular)<br>Purified Water | Granulate<br>↓<br>Dry<br>↓<br>Parcel size reduction | High shear granulator<br>(Littleford FM130)<br><br>Fluid bed drier<br>(Glatt fluid bed drier)<br>Mill<br>(Kemutec Betagrind) |

Niaspau® Granulation Process Description

Niaspan® granulation raw materials are dispensed and granulated in a high shear granulator. The wet granules are sieved into a fluid bed drier and are dried. When the drying process is complete, the granules are milled. Milling ensures uniform particle size distribution throughout the Niaspan® granulation.

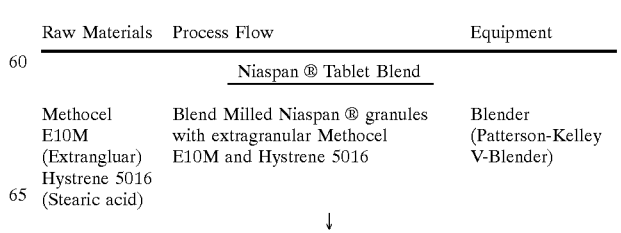

| Niaspan ® Tablet Process Flow Chart | | |
|---|---|---|
| Raw Materials | Process Flow | Equipment |
| | Niaspan ® Tablet Blend | |
| Methocel E10M (Extrangluar)<br>Hystrene 5016<br>(Stearic acid) | Blend Milled Niaspan ® granules with extragranular Methocel E10M and Hystrene 5016<br>↓ | Blender<br>(Patterson-Kelley V-Blender) |

Niaspan® Tablet Process Flow Chart

| Raw Materials | Process Flow | Equipment |
|---|---|---|
| | Niaspan® Tablet Manufacture | |
| | Compress Niaspan® Tablet Blend | Rotary tablet press |

Niaspan® Tablet Process Description

A Niaspans tablet blend is manufactured by blending the Niaspan® granulation, extragranular Methocel ELOM and Hystrene 5016. The quantities of each Niaspan® tablet blend component will depend on the particular Niaspan® dose being manufactured (refer to Table IB). A Niaspan® tablet blend is compressed to formn Niaspan® tablets. Niaspan® tablet physical properties will vary depending on the particular Niaspan® dose being manufactured.

Production of Niaspan® tablets will now be discussed in greater detail. The initial stage of manufacturing is the same for all four tablet strengths of Niaspan® (375, 500, 750, and 1000 mg). One batch of Niaspan® granulation is comprised of four individual 40.0 kg units of granulation which are processed separately, but under like conditions. The four individual granulations are sampled and tested individually and subsequently released for blending. The base granulation is not strength specific and may be used to manufacture any tablet strength of Niaspan®.

The ingredients in the base granulation are set forth in Table IC below:

TABLE IC

| Component | Function | Quantity per kilogram granulation (kg) | % per kilogram granulation (%) | Quantity per 160.00 kg batch (kg) |
|---|---|---|---|---|
| Niacin, USP | Drug Substance | 0.87 | 87.00 | 139.20 |
| Povidone, USP | Binder | 0.03 | 3.00 | 4.80 |
| Methocel USP, E10M Premium CR Grade | Controlled-Release Agent | 0.10 | 10.00 | 16.00 |
| Purified Water, USP* | Granulation Reagent | 0.00* | 0.00* | 48.00 |
| Total | | | | 160.00 |

*Purified Water, USP is used as a granulation reagent and does not appear in the finished granulation.

Raw materials are quantatively dispensed into appropriately labeled double polyethylene-lined containers using calibrated scales. Purified Water, USP is dispensed into an appropriate vessel from which it is later pumped during the wet-massing operation.

A Littleford FM130 granulator is charged with approximately one half of the Niacin, USP required for the process unit (~17.4 kg) followed by about 4.00 kg of Methocel, USP E10M Premium CR Grade; about 1.20 kg of Povidone, USP; and the balance of the Niacin, SP (~17.40 kg). The powder bed is dry mixed in the Littleford FM130 granulator, with choppers on, for approximately 1 minute. At the completion of the 1-minute pre-mix cycle, about 12.0±0.05 kg of Purified Water, USP are sprayed onto the powder bed at a rate of about 2.40±0.24 kg/minute. Immediately following the addition of the Purified Water, USP, the unit is granulated for about 5 minutes.

The granulated unit is discharged into double polyethylene-lined containers and then manually loaded into a Glatt bowl while being passed through a #4 mesh screen. the Glatt bowl is loaded into a Glatt TFO-60 fluid-bed drier with an inlet air temperature setting of about 70° C.±5° C. The unit is dried until a moisture level of $\leq 1.0\%$ is obtained as determined using a Computrac® Moisture Analyzer, model MA5A. The dried granulation is discharged into appropriately labeled, double polyethylene-lined drums and reconciled.

The dried and reconciled granulation is passed through a Kemutec BetaGrind mill equipped with a 1.5 mm screen and running at approximately 1500 RPM. The milled granulation is collected into appropriately labeled, double polyethylene-lined drums and reconciled. The milled granulation is sampled and tested by Quality Control and released prior to further processing.

The released granulation units are charged to a Patterson-Kelley 20 ft$^3$ V-blender after which they are blended together for about 10±1 minutes and then discharged to appropriately labeled, double polyethylene-lined containers.

As stated above, Niaspan® tablets are formulated from a common granulation which is blended with appropriate quantities of Methocel, USP E10M Premium CR Grade and Stearic Acid, NF to achieve the final dosage formulation. Tables IA and IB describe the formulation for each Niaspan® tablet strength, 375 mg, 500 mg, 750 mg, and 1000 mg, respectively.

Two study groups consisting of eleven and fourteen patients each were formed. Blood samples were taken from the patients, and tested for total cholesterol, LDL cholesterol, triglycerides and HDL cholesterol to establish baseline levels from which fluctuations in these lipids could be compared. The patients were then placed upon a regimen of the above discussed tablets, totalling approximately 1500 mg of nicotinic acid, once per day before going to bed. After eight weeks of this regimen, the patients were again tested for lipid profiles. The results of the tests conducted at eight weeks, showing the changes in the lipid profiles as a percentage change from the baseline, are reported in the table hereinbelow. Positive numbers reflect percentage increases and negative numbers reflect percentage decreases in this table.

TABLE II

Patient Study Lipid Profile Data

| Pt. No. | Total-C | LDL-C | Apo B | Trigs | HDL-C | $HDL_7$-C | Lp(a) |
|---|---|---|---|---|---|---|---|
| GROUP A | | | | | | | |
| 1 | −8.2 | −12.0 | NA | −17.3 | 22.0 | NA | NA |
| 2 | 5.9 | −27.0 | NA | −28.7 | 65.0 | NA | NA |
| 3 | −15.1 | −13.0 | NA | −22.0 | −9.1 | NA | NA |
| 4 | −3.3 | 10.0 | NA | 61.6 | 3.8 | NA | NA |
| 5 | −16.5 | −17.7 | NA | −28.8 | 11.1 | NA | NA |
| 6 | −12.4 | −25.9 | NA | 42.0 | 51.6 | NA | NA |
| 7 | −24.2 | −31.4 | NA | −39.4 | 12.5 | NA | NA |
| 8 | −6.7 | 7.4 | NA | 42.4 | 18.8 | NA | NA |
| 9 | 4.5 | 1.1 | NA | 7.2 | 9.2 | NA | NA |
| 10 | 2.8 | −0.2 | NA | −2.7 | 22.9 | NA | NA |
| 11 | −13.0 | −9.4 | NA | −54.0 | 44.3 | NA | NA |
| Mean | −8.9 | −13.9 | NA | −18.9 | 23.0 | NA | NA |
| p-Value | 0.0004 | 0.0001 | | 0.0371 | 0.0068 | | |
| GROUP B | | | | | | | |
| 1 | −19.2 | −27.1 | −24.4 | −33.4 | 20.0 | 22.3 | −81.9 |
| 2 | −32.2 | −35.7 | −28.0 | −60.4 | 4.3 | 3.2 | −25.3 |
| 3 | −21.4 | −33.6 | −35.6 | −33.4 | 30.4 | 38.6 | −17.4 |
| 4 | 19.9 | −24.6 | 15.1 | −20.8 | 9.6 | 16.1 | −27.0 |
| 5 | 3.3 | −2.1 | −29.4 | 41.1 | 5.8 | 2.4 | −22.4 |
| 6 | PATIENT WITHDREW FROM STUDY | | | | | | |
| 7 | 23.1 | −32.6 | −42.6 | −58.6 | 49.2 | 68.9 | −14.3 |
| 8 | 24.8 | 34.0 | −28.4 | 5.5 | 6.5 | −6.8 | NA |
| 9 | 10.1 | 12.0 | −16.8 | −11.6 | 20.7 | −12.3 | 40.6 |
| 10 | −2.9 | 7.7 | −28.0 | −59.0 | 53.1 | 70.5 | A1.2 |
| 11 | −10.5 | −18.8 | −25.3 | −53.4 | 31.8 | 39.7 | NA |
| 12 | −20.0 | −30.8 | −30.4 | 11.7 | 21.1 | 25.0 | −28.4 |
| 13 | 17.4 | 16.8 | −17.5 | −17.5 | 51.3 | 51.9 | 38.5 |
| 14 | −9.4 | −16.6 | −32.0 | 46.9 | 52.3 | 67.6 | 17.6 |
| Mean | −8.7 | −12.8 | −32.2 | −27.2 | 25.3 | 30.1 | −17.9 |
| p-Value | 0.0002 | <0.0001 | 0.0001 | <0.001 | <0.0001 | 0.0002 | <0.0188 |
| Combined | −8.7 | −13.3 | Gp B | −26.1 | 25.3 | Gp B | Gp B |
| p-Value | 0.0002 | <0.0001 | only | <.0001 | <0.0001 | only | only |

The data reported in TABLE II shows that the LDL levels in the Group A patients had a mean decrease of −13.9% and triglyceride decrease of −18.9% HDL cholesterol levels, the beneficial cholesterol, were raised by 23.0% in this Group. Similar results were obtained with the Group B patients. These studies demonstrate that dosing the sustained release formulation during the evening hours or at night provides reductions in LDL cholesterol levels equal to immediate release niacin on a milligram per milligram basis, but superior reductions in triglyceride reductions when compared to sustained release formulations dosed during daytime hours on a milligram per milligram basis. Additionally, the increases in HDL cholesterol obtained from dosing the sustained release formulation during the evening or at night were +23.0% for one group and +25.3 % for the other group. Dosing during the evening therefore provides reduction in LDL cholesterol plus significant decreases in triglycerides and increases in HDL cholesterol with once-a-day dosing.

Groups A and B were also tested for liver enzymes (AST, ALT and Alkaline Phosphatase), uric acid and fasting glucose levels at the start of the study described hereinabove (to form a baseline) and at two, four and eight week intervals. The results of these tests are listed in TABLES VI–VII hereinbelow.

TABLE III

THE EFFECT OF NIASPAN ® THERAPY ON AST
(SGOT) LEVELS (U/L)
(1500 mgs dosed once-a-day at night)
(n = 28)

| | | Weeks of Therapy With NIASPAN ™ | | | |
|---|---|---|---|---|---|
| Pt # | Baseline | 2 Wks. | 4 Wks. | 8 Wks. | Reference Range |
| GROUP A | | | | | |
| 1 | 28 | 29 | 25 | 24 | 0–50 |
| 2 | 24 | 25 | 24 | 26 | 0–50 |
| 3 | 17 | 18 | 22 | 21 | 0–50 |
| 4 | 14 | 16 | 15 | 17 | 0–50 |
| 5 | 22 | NA | 32 | 52 | 0–50 |
| 6 | 21 | 17 | 17 | 14 | 0–50 |
| 7 | 17 | 17 | 14 | 18 | 0–50 |
| 8 | 20 | 21 | 22 | 22 | 0–50 |
| 9 | 16 | 16 | 17 | 20 | 0–50 |
| 10 | 18 | 21 | 21 | 25 | 0–50 |
| 11 | 21 | 21 | 22 | 21 | 0–50 |
| GROUP B | | | | | |
| 1 | 23 | 25 | 38 | 33 | 0–50 |
| 2 | 20 | 20 | 21 | 21 | 0–50 |
| 3 | 15 | 20 | 18 | 19 | 0–50 |
| 4 | 25 | 22 | 25 | 26 | 0–50 |
| 5 | 23 | 21 | 17 | 18 | 0–50 |
| 6 | PATIENT WITHDREW DUE TO FLUSHING | | | | |
| 7 | 21 | 18 | 18 | 19 | 0–50 |
| 8 | 18 | 19 | 18 | 19 | 0–50 |

TABLE III-continued

THE EFFECT OF NIASPAN ® THERAPY ON AST
(SGOT) LEVELS (U/L)
(1500 mgs dosed once-a-day at night)
(n = 28)
Weeks of Therapy With NIASPAN ™

| Pt # | Baseline | 2 Wks. | 4 Wks. | 8 Wks. | Reference Range |
|---|---|---|---|---|---|
| 9 | 15 | 16 | 18 | 15 | 0–50 |
| 10 | 16 | 15 | 19 | 28 | 0–50 |
| 11 | 20 | 22 | 24 | 28 | 0–50 |
| 12 | 23 | 25 | 28 | 22 | 0–50 |
| 13 | 20 | 15 | 20 | 19 | 0–50 |
| 14 | 18 | 25 | 20 | 18 | 0–50 |
| Combined Mean | 19.8 | 20.4 | 20.8 | 21.1 | |
| Change From Baseline | | +3.0% | +5.1% | +6.6% | |

Level of Significance: p = 0.4141

TABLE IV

THE EFFECT OF NIASPAN ® THERAPY ON ALT
(SGPT) LEVELS (U/L)
(1500 mgs dosed once-a-day at night)
(n = 28)
Weeks of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 32 | 28 | 39 | 30 | 0–55 |
| 2 | 24 | 25 | 23 | 26 | 0–55 |
| 3 | 18 | 23 | 30 | 30 | 0–55 |
| 4 | 7 | 13 | 14 | 14 | 0–55 |
| 5 | 14 | NA | 43 | 46 | 0–55 |
| 6 | 22 | 11 | 14 | 10 | 0–55 |
| 7 | 9 | 7 | 11 | 7 | 0–55 |
| 8 | 16 | 18 | 23 | 21 | 0–55 |
| 9 | 14 | 17 | 20 | 14 | 0–55 |
| 10 | 14 | 15 | 17 | 19 | 0–55 |
| 11 | 18 | 18 | 20 | 16 | 0–55 |
| GROUP B | | | | | |
| 1 | 16 | 17 | 27 | 29 | 0–55 |
| 2 | 16 | 14 | 15 | 22 | 0–55 |
| 3 | 13 | 21 | 13 | 16 | 0–55 |
| 4 | 23 | 20 | 26 | 17 | 0–55 |
| 5 | 21 | 23 | 17 | 15 | 0–55 |
| 6 | PATIENT WITHDREW DUE TO FLUSHING | | | | |
| 7 | 21 | 16 | 18 | 21 | 0–55 |
| 8 | 18 | 20 | 17 | 18 | 0–55 |
| 9 | 11 | 5 | 11 | 8 | 0–55 |
| 10 | 8 | 10 | 14 | 17 | 0–55 |
| 11 | 17 | 12 | 18 | 16 | 0–55 |
| 12 | 14 | 18 | 20 | 16 | 0–55 |
| 13 | 14 | NA | 11 | 10 | 0–55 |
| 14 | 23 | 23 | 19 | 19 | 0–55 |
| Combined Mean | 17.7 | 17.5 | 19.3 | 18.2 | |
| Change From Baseline | | −1.1% | 9.0% | +2.8% | |

Level of Significance: p = 0.3424

TABLE V

THE EFFECT OF NIASPAN ® THERAPY
ON ALKALINE PHOSPHATASE LEVELS (U/L)
(1500 mgs dosed once-a-day at night)
(n = 28)
Weeks Of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 52 | 56 | 57 | 55 | 20–140 |
| 2 | 103 | 100 | 89 | 102 | 20–140 |
| 3 | 54 | 45 | 53 | 51 | 20–140 |
| 4 | 70 | 68 | 71 | 91 | 20–140 |
| 5 | 77 | NA | 74 | 81 | 20–140 |
| 6 | 55 | 48 | 49 | 51 | 20–140 |
| 7 | 72 | 71 | 79 | 75 | 20–140 |
| 8 | 55 | 49 | 47 | 50 | 20–140 |
| 9 | 53 | 55 | 56 | 45 | 20–140 |
| 10 | 74 | 73 | 75 | 75 | 20–140 |
| 11 | 18 | 18 | 20 | 16 | 20–140 |
| GROUP B | | | | | |
| 1 | 73 | 67 | 89 | 95 | 20–140 |
| 2 | 82 | 64 | 72 | 71 | 20–140 |
| 3 | 73 | 69 | 72 | 82 | 20–140 |
| 4 | 37 | 36 | 37 | 38 | 20–140 |
| 5 | 65 | 53 | 54 | 61 | 20–140 |
| 6 | PATIENT WITHDREW DUE TO FLUSHING | | | | |
| 7 | 64 | 58 | 58 | 58 | 20–140 |
| 8 | 79 | 78 | 65 | 73 | 20–140 |
| 9 | 94 | 92 | 103 | 93 | 20–140 |
| 10 | 69 | 67 | 70 | 65 | 20–140 |
| 11 | 59 | 67 | 63 | 72 | 20–140 |
| 12 | 65 | 59 | 59 | 63 | 20–140 |
| 13 | 64 | 68 | 66 | 64 | 20–140 |
| 14 | 72 | 61 | 59 | 64 | 20–140 |
| Combined Mean | 66.5 | 61.5 | 63.3 | 65.8 | |
| Change From Baseline | | −6.1% | −3.4% | +0.005% | |

Level of Significance: p = 0.0236

TABLE VI

THE EFFECT OF NIASPAN ® THERAPY ON URIC
ACID LEVELS (mg/dL)
(1500 mgs dosed once-a-day at night)
(n = 28)
Weeks Of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 5.2 | 5.0 | 4.8 | 4.3 | 4.0–8.5 |
| 2 | 4.0 | 4.6 | 4.5 | 6.2 | 2.5–7.5 |
| 3 | 6.3 | 7.0 | 6.5 | 6.2 | 4.0–8.5 |
| 4 | 3.1 | 4.6 | 4.2 | 3.8 | 2.5–7.5 |
| 5 | 3.4 | NA | 3.3 | 4.2 | 2.5–7.5 |
| 6 | 6.6 | 5.5 | 5.6 | 4.7 | 4.0–8.5 |
| 7 | 3.8 | 4.5 | 4.3 | 4.9 | 2.5–7.5 |
| 8 | 4.4 | 3.8 | 5.1 | 4.5 | 2.5–7.5 |
| 9 | 3.9 | 4.5 | 4.6 | 3.5 | 2.5–7.5 |
| 10 | 2.6 | 2.9 | 2.8 | 2.7 | 2.5–7.5 |
| 11 | 4.7 | 5.5 | 5.2 | 5.3 | 2.5–7.5 |
| GROUP B | | | | | |
| 1 | 3.7 | 4.2 | 4.7 | 3.5 | 2.5–7.5 |
| 2 | 2.8 | 3.5 | 3.6 | 2.3 | 4.0–8.5 |
| 3 | 4.2 | 5.3 | 5.5 | 5.3 | 2.5–7.5 |
| 4 | 4.7 | 3.9 | s.i | 3.6 | 4.0–8.5 |
| 5 | 3.7 | 4.1 | 4.1 | 3.8 | 2.5–7.5 |

TABLE VI-continued

THE EFFECT OF NIASPAN ® THERAPY ON URIC
ACID LEVELS (mg/dL)
(1500 mgs dosed once-a-day at night)
(n = 28)
Weeks Of Therapy With NIASPAN ®

| Pt # | Baseline | 2 Wks. | 4 Wks. | 8 Wks. | Reference Range |
|---|---|---|---|---|---|
| 6 | PATIENT WITHDREW DUE TO FLUSHING | | | | |
| 7 | 5.8 | 6.6 | 6.6 | 6.8 | 2.5–7.5 |
| 8 | 4.7 | 4.3 | 5.4 | 5.6 | 2.5–7.5 |
| 9 | 3.7 | 4.6 | 5.1 | 3.8 | 2.5–7.5 |
| 10 | 4.2 | 5.0 | 4.4 | 8.5 | 2.5–7.5 |
| 11 | 1.9 | 3.0 | 2.8 | 5.0 | 2.5–7.5 |
| 12 | 5.6 | 5.4 | 6.2 | 5.6 | 4.0–8.5 |
| 13 | 4.2 | 4.6 | 4.6 | 5.3 | 2.5–7.5 |
| 14 | 5.5 | 5.4 | 6.1 | 5.3 | 2.5–7.5 |
| Combined Mean | 4.54 | 4.82 | 4.92 | 4.86 | *p = 0.3450 |
| Change From Baseline | | +6.2% | +8.4% | +7.0% | |

*Level of Significance: p = 0.3450

TABLE VII

THE EFFECT OF NIASPAN ® THERAPY
ON FASTING GLUCOSE LEVELS (mg/dL)
(1500 mgs dosed once-a-day at night)
(n = 28)
Weeks Of Therapy With NIASPAN ®

| Pt # | Baseline | 2 Wks. | 4 Wks. | 8 Wks. | Reference Range |
|---|---|---|---|---|---|
| GROUP A | | | | | |
| 1 | 114 | 122 | 123 | 110 | 70–115 |
| 2 | 101 | 105 | 107 | 101 | 80–125 |
| 3 | 99 | 98 | 109 | 103 | 70–115 |
| 4 | 100 | 118 | 94 | 94 | 80–125 |
| 5 | 89 | NA | 82 | 103 | 80–125 |
| 6 | 97 | 103 | 94 | 107 | 70–115 |
| 7 | 85 | 107 | 100 | 94 | 80–125 |
| 8 | 98 | 107 | 103 | 101 | 80–125 |
| 9 | 97 | 97 | 100 | 110 | 80–125 |
| 10 | 94 | 101 | 111 | 97 | 70–115 |
| 11 | 102 | 103 | 95 | 95 | 80–125 |
| GROUP B | | | | | |
| 1 | 101 | 97 | 83 | 99 | 70–115 |
| 2 | 90 | 95 | 96 | 89 | 80–125 |
| 3 | 96 | 98 | 95 | 97 | 70–115 |
| 4 | 116 | 139 | 113 | 125 | 80–125 |
| 5 | 88 | 92 | 91 | 95 | 70–115 |
| 6 | PATIENT WITHDREW DUE TO FLUSHING | | | | |
| 7 | 106 | 114 | 118 | 117 | 70–115 |
| 8 | 95 | 106 | 106 | 108 | 70–115 |
| 9 | 81 | 92 | 84 | 92 | 70–115 |
| 10 | 108 | 117 | 122 | 105 | 70–11S |
| 11 | 85 | 106 | 106 | 108 | 70–115 |
| 12 | 92 | 89 | 101 | 86 | 80–125 |
| 13 | 99 | 105 | 94 | 100 | 70–125 |
| 14 | 100 | 108 | 84 | 107 | 70–125 |
| Combined Mean | 98.4 | 105.8 | 101.6 | 102.3 | |
| Change From Baseline | | +7.5% | +3.3% | +4.0% | |

Level of Significance: p = 0.0021

In order to provide a comparison between the state of the art prior to the present invention, and in order to quantify the magnitude of the improvement that the invention provides over the prior art, another study was conducted. This study included 240 patients dosed according to the present invention as described hereinabove. Compared to this group was the group of patients studied by McKenney et al., as reported hereinabove. The results of this study are reported in TABLE VIII hereinbelow.

TABLE VIII

A Comparison of Changes in Liver Function Tests

| | DOSE | | | | | | | |
|---|---|---|---|---|---|---|---|---|
| | 0 | 500 | 1000 | 1500 | 2000 | 2500 | 3000 | TOTAL |
| McKenney SR[b] Niacin[a] | | | | | | | | |
| AST | 23.8 | 27.9 | 40.4 | 36.6 | 56.5 | na | 97.0 | |
| % | — | 117 | 170 | 154 | 237 | na | 408 | |
| Invention Dosage[c] | | | | | | | | |
| AST | 24.3 | na | 23.7 | 27.5 | 26.6 | 27.6 | 27.8 | |
| % | — | na | 98 | 113 | 109 | 114 | 114 | |
| McKenney SR Niacin | | | | | | | | |
| ALT | 25.6 | 29.5 | 36.3 | 39.0 | 59.1 | na | 100.0 | |
| % | — | 115 | 142 | 152 | 231 | na | 391 | |
| Invention Dosage | | | | | | | | |
| ALT | 21.4 | na | 18.7 | 22.6 | 21.3 | 22.4 | 21.8 | |
| % | — | na | 87 | 106 | 100 | 105 | 102 | |
| McKenney SR Niacin | | | | | | | | |
| ALK | 95 | 95 | 106 | 105 | 136 | na | 135 | |
| % | — | 100 | 112 | 111 | 143 | na | 142 | |
| Invention Dosage | | | | | | | | |
| ALK | 74.7 | na | 73.9 | 76.1 | 73.4 | 76.7 | 78.0 | |
| % | — | na | 99 | 102 | 98 | 103 | 104 | |
| McKenney SR Niacin | | | | | | | | |
| Drop | — | 0 | 2 | 2 | 7 | na | 7 | 18 |
| n | — | — | — | — | — | — | — | 23 |
| % | — | 0 | 9 | 9 | 30 | na | 30 | 78 |
| Invention Dosage | | | | | | | | |
| Drop | — | — | 0 | 0 | 0 | 0 | 0 | 0 |
| n | — | — | 26 | 67 | 97 | 35 | 15 | 240 |
| % | — | — | 0 | 0 | 0 | 0 | 0 | 0 |
| 1 year | — | — | 15 | 46 | 77 | 31 | 15 | 184 |
| 1 year | — | — | 58 | 69 | 79 | 89 | 100 | 77 |

[a]Dosed twice-per-day as described in "A Comparison of the Efficacy and Toxic Effects of Sustained - vs Immediate - Release Niacin in Hypercholesterolemic Patients" by McKenney et al. Journal of the American Medial Association, March 2, 1994; Vol. 271, No. 9, pages 672–677.
[b]SR is "sustained release"
[c]Dosed once-per-day at night The results of the comparison of the studies reported in TABLE VIII show that the control group (the McKenney group) had 18 of 23, or 78 percent of the patients therein drop out of the test because of an increase in their respective liver function tests. The patients withdrew at the direction of the investigator. In comparison, a group of 240 patients treated according to the present invention had zero patients drop out, based upon the same criteria for withdrawal. The tests results reported above indicate that this sustained release dosage form caused no elevation in liver function tests (i.e., no liver damage), no elevations in uric acid and only a small, 7.5% increase in fasting glucose levels which in fact decreased during continued therapy.

Thus it should be evident that the compositions and method of the present invention are highly effective in controlling hyperlipidemia in hyperlipidemics, by reducing the levels of LDL cholesterol, triglyceride and Lp(a) while increasing HDL cholesterol levels. The present invention is also demonstrated not to cause elevations in liver function tests, uric acid or glucose levels for the hyperlipidemics.

Based upon the foregoing disclosure, it should now be apparent that the use of the compositions and methods described herein will carry out the objects set forth hereinabove. It is, therefore, to be understood that any variations in sustained release formulation evident fall within the scope of the claimed invention and thus, the selection of specific component elements can be determined without departing from the spirit of the invention herein disclosed and described. In particular, sustained release excipients, binders and processing aids according to the present invention are not necessarily limited to those exemplified hereinabove. Thus, the scope of the invention shall include all modifications and variations that my fall within the scope of the attached claims.

What is claimed is:

1. A daily method of treating hyperlipidemia in a patient comprising orally administering to the patient a sustained release composition of nicotinic acid once per day during the evening for providing an effective antihyperidemic amount of nicotinic acid to the patient to induce at least some lowering of total cholesterol, LDL cholesterol, triglycerides and Lp(a) and at least some increase in HDL cholesterol in the patient's blood stream, without causing abnormalities in uric acid levels or glucose levels or both to an extent which would require said daily treatment to be discontinued by the patient, the sustained release composition comprising an effective antihyperlipidemic amount of nicotinic acid and an excipient to provide sustained release of the nicotinic acid.

2. A method of claim 1, wherein the effective antihyperlipidemic amount of nicotinic acid is from about 250 mg to about 3000 mg of nicotinic acid.

3. A method of claim 1, wherein the excipient is selected from the group consisting of a swelling agent, a binder, a processing aid and mixtures thereof.

4. A method of claim 3, wherein the swelling agent is selected from group consisting of a polymer, a wax, a natural material and mixtures thereof.

5. A method of claim 4, wherein the polymer is selected from the group consisting of hydroxypropyl methylcellulose, sodium carboxymethylcellulose and ethylcellulose.

6. A method of claim 4, wherein the wax is bees wax.

7. A method of claim 4, wherein the natural material is selected from the group consisting of gums and gelatins.

8. A method of claim 3, wherein the binder is povidone.

9. A method of claim 3, wherein the processing aid is a lubricant.

10. A method of claim 9, wherein the lubricant is stearic acid.

11. A method of claim 5, wherein the hydroxypropyl methylcellulose is in an amount ranging from about 5% to about 50% parts by weight per 100 parts by weight of the sustained release composition.

12. A method of claim 3, wherein the binder is in an amount ranging from about 1% to about 5% parts by weight per 100 parts by weight of the sustained release composition.

13. A method of claim 3, wherein the processing aid is in an amount ranging from about 0.5% to about 2% parts by weight per 100 parts by weight of the sustained release composition.

14. A method of claim 1, wherein the sustained release composition consists essentially of nicotinic acid, hydroxypropyl methylcellulose, povidone and stearic acid.

15. A method of claim 1, wherein the sustained release composition consists essentially of
   nicotinic acid 375.0 mg,
   hydroxypropyl methylcellulose 188.75 mg,
   povidone 12.9 mg., and
   stearic acid 5.8 mg.

16. A method of claim 1, wherein the sustained release composition consists essentially of
   nicotinic acid 500.0 mg,
   hydroxypropyl methylcellulose 203.0 mg,
   povidone 17.2 and
   stearic acid 7.3.

17. A method of claim 1, wherein the sustained release composition consists essentially of
   nicotinic acid 750.0
   hydroxypropyl methylcellulose 204.7
   povidone 25.9 and
   stearic acid 9.9.

18. A sustained release composition of nicotinic acid for oral administration to a patient once per day during the evening or at night for providing and effective antihyperlipidemic amount of nicotinic acid to the patient to induce at least some lowering of total cholesterol, LDL cholesterol, triglycerides and Lp(a) and at least some increase in HDL cholesterol in the patient's blood stream, without causing abnormalities in uric acid levels or glucose levels or both to an extent which would require the use of said release composition by the patient to be discontinued, said sustained release composition comprising (a) an effective antihyperlipidemic amount of nicotinic acid, and (b) an excipient to provide sustained release of the nicotinic acid.

19. A sustained release composition of claim 18, wherein said excipient is selected from the group consisting of a swelling agent, a binder, a processing aid and mixtures thereof.

20. A sustained release composition of claim 19, wherein the swelling agent is selected from group consisting of a polymer, a wax, a natural material and mixtures thereof.

21. A sustained release composition of claim 20, wherein the polymer is selected from the group consisting of hydroxypropyl methylcellulose, sodium carboxymethylcellulose and ethylcellulose.

22. A sustained release composition of claim 20, wherein the wax is bees wax.

23. A sustained release composition of claim 20, wherein the natural material is selected from the group consisting of gums and gelatins.

24. A sustained release composition of claim 19, wherein the binder is povidone.

25. A sustained release composition of claim 19, wherein the processing aid is a lubricant.

26. A sustained release composition of claim 25, wherein the lubricant is stearic acid.

27. A sustained release composition of claim 21, wherein the hydroxypropyl methylcellulose is in an amount ranging from about 5% to about 50% parts by weight per 100 parts by weight of the sustained release composition.

28. A sustained release composition of claim 19, wherein the binder is in an amount ranging from about 1% to about 5% parts by weight per 100 parts by weight of the sustained release composition.

29. A sustained release composition of claim 19, wherein the processing aid is in an amount ranging from about 0.5% to bout 2% parts by weight per 100 parts by weight of the sustained release composition.

30. A sustained release composition of claim 18, wherein the sustained release composition consists essentially of nicotinic acid, hydroxypropyl methylcellulose, povidone and stearic acid.

31. A sustained release composition of claim 18, wherein the sustained release composition consists essentially of nicotinic acid 375.0 mg, hydroxypropyl methylcellulose 188.7 mg, povidone 12.9 mg., and stearic acid 5.8 mg.

32. A sustained release composition of claim 18, wherein the sustained release composition consists essentially of nicotinic acid 500.0 mg, hydroxypropyl methylcellulose 203.0 mg, povidone 17.2 mg., and stearic acid 7.3 mg.

33. A sustained composition of claim 18, wherein the sustained release composition consists essentially of nicotinic acid 750.0 mg, hydroxypropyl methylcellulose 204.7 mg, povidone 25.9 mg., and stearic acid 9.9 mg.

34. A daily method of treating hyperlipidemia in a patient without inducing treatment-limiting elevations in uric acid levels or glucose levels or both in the patient, said daily method comprising orally dosing the patient with an effective antihyperlipidemic amount of nicotinic acid once per day during the evening or at night as a dose, wherein the nicotinic acid is combined with at least one pharmaceutically acceptable carrier to form an oral sustained release solid dosage form.

35. A method, as set forth in claim 34, wherein the patient is dosed with from about 250 mg to about 3000 mg of nicotinic acid.

36. A method, as set forth in claim 35, wherein the release rate of the nicotinic acid is from about 2.0% per hour to about 25% per hour.

37. A method, as set forth in claim 34, wherein the oral sustained release solid dosage form is prepared by formulating the nicotinic acid with from about 5 parts to about 50 parts by weight of hydroxypropyl methylcellulose per 100 parts by weight of the oral sustained release solid dosage form.

38. A method, as set forth in claim 34, wherein the oral sustained release solid dosage form contains from about 1 part to about 4 parts by weight of binder per 100 parts by weight of the oral sustained release solid dosage form.

39. A method, as set forth in claim 36, wherein the binder is a polymer having the repeating polymerization unit 1-ethenyl-2-pyrrolidone.

40. A method, as set forth in claim 34, wherein the oral sustained release solid dosage form contains from abut 0.5 parts to abut 2.5 parts by weight of a lubricant per 100 parts by weight of the oral sustained release solid dosage form.

41. A method, as set forth in claim 40, wherein the lubricant is selected from the group consisting of lubricants consisting of stearic acid and magnesium stearate.

42. A method, as set forth in claim 34, wherein the oral sustained release solid dosage form contains from about 250 mg to about 3000 mg of nicotinic acid.

43. A method, as set forth in claim 34, wherein the oral sustained release solid dosage form is an oral sustained release tablet.

44. A method, as set forth in claim 43, wherein the oral sustained release tablet contains nicotinic acid in an amount selected from the group consisting of about 375 mg, about 500 mg and about 750 mg.

45. A method, as set forth in claim 43, wherein the oral sustained release tablet contains (a) about 375 mg nicotinic acid, (b) about 189 mg hydroxypropyl methylcellulose as a swelling agent (c) about 13 mg a polymer having the repeating polymerization unit 1-ethenyl-2-pyrrolidone as a binder, and (d) about 6 mg of stearic as a lubricant.

46. A method, as set forth in claim 43, wherein the oral sustained release tablet contains (a) about 500 mg nicotinic acid, (b) about 203 mg hydroxypropyl methylcellulose as a swelling agent (c) about 17.2 mg polyvinyl pyrrolidone as a binder, and (d) about 7.3 mg of stearic as a lubricant.

47. A method, as set forth in claim 43, wherein the oral sustained release tablet contains (a) about 750 mg nicotinic acid, (b) about 205 mg hydroxypropyl methylcellulose as a swelling agent (c) about 26 mg polyvinyl pyrrolidone as a binder, and (d) about 10 mg of stearic as a lubricant.

48. A method, as set forth in claim 43, wherein the oral sustained release tablet contains (a) about 30% to about 90% by weight nicotinic acid, (b) about 5% to about 50% by weight hydroxypropyl methylcellulose as a swelling agent, (c) about 1% to about 5% by weight a polymer having repeating polymerization unit 1-ethenyl-2-pyrrolidone as a binder, and (d) about 0.5% to about 2% by weight stearic acid as a lubricant.

49. A method, as set forth in claim 43, wherein the oral sustained release tablet contains (a) about 30% to about 90% by weight nicotinic acid, (b) about 5% to about 50% by weight hydroxypropyl methylcellulose as a swelling agent.

50. A method, as set forth in claim 34, wherein said single dose treatment during the evening or at night elevates HDL cholesterol in the patient.

51. A daily method of treating hyperlipidemia in a patient without inducing treatment-limiting abnormalities in uric acid levels or glucose levels or both in the patient, said daily method comprising orally dosing the patient with an effective antihyperlipidemic amount of nicotinic acid once per day during the evening or at night as a single dose for providing an effective antihyperlipidemic amount of nicotinic acid to the patient to induce at least some decrease in levels of total cholesterol, LDL cholesterol, triglycerides and Lp(a) in the patient and to induce at least some increase in levels of HDL cholesterol in the patient, without causing abnormalities in either uric acid or glucose levels or both to an extent which would require said daily treatment to be discontinued by the patient, wherein the nicotinic acid is combined with at least one pharmaceutically acceptable component to form an oral sustained release solid dosage form.

52. A method, as set forth in claim 51, wherein said single dose treatment induces at least some decrease in levels of total cholesterol, LDL cholesterol, triglycerides and Lp(a) in the patient.

53. A method, as set forth in claim 51, wherein said single dose treatment elevates HDL cholesterol in the patient.

54. A method of treating hyperlipidemia in a human without causing treatment-limiting elevations in uric acid levels or glucose levels or both in the human, said daily treatment comprising ingesting an oral sustained release nicotinic acid tablet once per day as a single dose for providing an effective antihyperlipidemic amount of nicotinic acid to the human without causing treatment-limiting elevations in uric acid or glucose levels or both in the human, wherein the nicotinic acid is combined with at least one pharmaceutically acceptable component to form the oral sustained release tablet.

55. A method, as set forth in claim 54, wherein said single dose treatment induces at least some decrease in levels of total cholesterol, LDL cholesterol, triglycerides and Lp(a) in the human.

56. A method, as set forth in claim 54, wherein said single dose treatment elevates HDL cholesterol in the human.

57. A daily method of treating hyperlipidemia in a patient without inducing treatment-limiting liver damage, said daily method comprising orally dosing the patient with an effective antihyperlipidemic amount of nicotinic acid once per day during the evening or at night as a single dose, wherein the nicotinic acid is combined with at least one pharmaceutically acceptable carrier to form an oral sustained release solid dosage form, said single daily dose treatment causing little or no serious damage to the liver of the patient.

58. A method, as set forth in claim 57, wherein the patient is dosed with from about 250 mg to about 3000 mg of nicotinic acid.

59. A method, as set forth in claim 58, wherein the release rate of the nicotinic acid is from about 2.0% per hour to about 25% per hour.

60. A method, as set forth in claim 58, wherein the oral sustained release solid dosage form is prepared by formulating the nicotinic acid with from about 5 parts to about 50 parts by weight of hydroxypropyl methylcellulose per 100 parts by weight of the oral sustained release solid dosage form.

61. A method, as set forth in claim 57, wherein the oral sustained release solid dosage form contains from about 1 part to about 4 parts by weight of binder per 100 parts by weight of the oral sustained release solid dosage form.

62. A method, as set forth in claim 59, wherein the binder is a polymer having the repeating polymerization unit 1-ethenyl-2-pyrrolidone.

63. A method, as set forth in claim 59, wherein the oral sustained release solid dosage form contains from about 0.5 parts to about 2.5 parts by weight of a lubricant per 100 parts by weight of the oral sustained release solid dosage form.

64. A method, as set forth in claim 63, wherein the lubricant is selected from the group consisting of lubricants consisting of stearic acid and magnesium stearate.

65. A method, as set forth in claim 57, wherein the oral sustained release solid dosage form contains from about 250 mg to about 3000 mg of nicotinic acid.

66. A method, as set forth in claim 57, wherein the oral sustained release solid dosage form is an oral sustained release tablet.

67. A method, as set forth in claim 66, wherein the oral sustained release tablet contains nicotinic acid in an amount selected from the group consisting of about 375 mg, about 500 mg and about 750 mg.

68. A method, as set forth in claim 66, wherein the oral sustained release tablet contains
(a) about 375 mg nicotinic acid,
(b) about 189 mg hydroxypropyl methylcellulose as a swelling agent
(c) about 13 mg a polymer having the repeating polymerization unit 1-ethenyl-2-pyrrolidone as a binder, and
(d) about 6 mg of stearic as a lubricant.

69. A method, as set forth in claim 66, wherein the oral sustained release tablet contains
(a) about 500 mg nicotinic acid,
(b) about 203 mg hydroxypropyl methylcellulose as a swelling agent
(c) about 17.2 mg polyvinyl pyrrolidone as a binder, and
(d) about 7.3 mg of stearic acid as a lubricant.

70. A method, as set forth in claim 66, wherein the oral sustained release tablet contains
(a) about 750 mg nicotinic acid,
(b) about 205 mg hydroxypropyl methylcellulose as a swelling agent
(c) about 26 mg polyvinyl pyrrolidone as a binder, and
(d) about 10 mg of stearic acid as a lubricant.

71. A method, as set forth in claim 66, wherein the oral sustained release tablet contains
(a) about 30% to about 90% by weight nicotinic acid,
(b) about 5% to about 50% by weight hydroxypropyl methylcellulose as a swelling agent,
(c) about 1% to about 5% by weight a polymer having repeating polymerization unit 1-ethenyl-2-pyrrolidone as a binder, and
(d) about 0.5% to about 2% by weight stearic acid as a lubricant.

72. A method, as set forth in claim 66, wherein the oral sustained release tablet contains
(a) about 30% to about 90% by weight nicotinic acid,
(b) about 5% to about 50% parts by weight hydroxypropyl methylcellulose as a swelling agent.

73. A method, as set forth in claim 57, wherein said single dose treatment during the evening or at night elevates HDL cholesterol in the patient.

74. A method, as set forth in claim 57, wherein said single dose treatment during the evening or at night results in little or no serious increase in a liver function test in the patient, wherein the liver function test is selected from the group consisting of an AST, ALT and alkaline phosphatase liver function test.

75. A method, as set forth in claim 57, wherein said single dose treatment during the evening or at night results in little or no serious increase in uric acid in the patient.

76. A method, as set forth in claim 57, wherein said single dose treatment during the evening or at night results in little or no serious increase in free fasting glucose in the patient.

77. A daily method of treating hyperlipidemia in a patient without inducing treatment-limiting hepatotoxicity, said daily method comprising orally dosing the patient with an effective amount of nicotinic acid once per day during the evening or at night as a single dose for reducing hyperlipidemia in the patient, wherein the nicotinic acid is combined with at least one pharmaceutically acceptable component to form an oral sustained release solid dosage form, and wherein said single daily nicotinic acid dose treatment administered during the evening or at night is at least as effective in lowering at least one serum lipid in a patient wherein the serum lipid is selected from the group consisting of total cholesterol, LDL cholesterol, triglycerides and Lp(a), as treatment with an oral sustained release nicotinic acid preparation when it is dosed daily in two divided doses at a total daily nicotinic acid dosage which is at least equivalent to said single daily nicotinic acid dose treatment administered only during the evening or at night, and wherein said single daily nicotinic acid dose treatment administered during the evening or at night is essentially free of treatment-limiting hepatotoxic side effects which are generally associated with the oral sustained release nicotinic acid preparation when it is dosed daily in two divided doses at a total daily nicotinic acid dosage which is at least equivalent to said single daily nicotinic acid dose treatment administered during the evening or at night.

78. A method, as set forth in claim 77, wherein the patient is dosed with from 250 mg to about 3000 mg of nicotinic acid.

79. A method, as set forth in claim 77, wherein the release rate of said nicotinic acid is from about 2.0% per hour to about 25% per hour.

80. A method, as set forth in claim 77, wherein the oral solid dosage form is prepared by formulating the nicotinic acid with from about 5 to about 50 parts by weight of hydroxypropyl methylcellulose per 100 parts by weight of the oral solid dosage form.

81. A method, as set forth in claim 77, wherein the oral solid dosage form further contains from about 1 to about 4 parts by weight of a binder per 100 parts by weight of the oral solid dosage form.

82. A method, as set forth in claim 81, wherein the binder is polyvinyl pyrrolidone.

83. A method, as set forth in claim 77, wherein the oral solid dosage form further contains from about 0.5 to about 2.5 parts by weight of a lubricant per 100 parts by eight of the solid dosage form.

84. A method, as set forth in claim 83, wherein the lubricant is selected from the group consisting of stearic acid and magnesium stearate.

85. A method, as set forth in claim 77, wherein the oral sustained release solid dosage form contains from about 250 mg to about 3000 mg of nicotinic acid.

86. A method, as set forth in claim 77, wherein the oral sustained release solid dosage form is an oral sustained release tablet.

87. A method, as set forth in claim 86, wherein the oral sustained released tablet contains nicotinic acid in an amount selected from the group consisting of about 375 mg, about 500 mg and about 750 mg.

88. A method, as set forth in claim 86, wherein the oral sustained release tablet contains
    (a) about 375 mg nicotinic acid,
    (b) about 189 mg hydroxypropyl methylcellulose as a swelling agent,
    (c) about 13 mg polyvinyl pyrrolidone as a binder, and
    (d) about 6 mg of stearic acid as a lubricant.

89. A method, as set forth in claim 86, wherein the oral sustained release tablet contains
    (a) about 500 mg nicotinic acid,
    (b) about 203 mg hydroxypropyl methylcellulose as a swelling agent,
    (c) about 17 mg polyvinyl pyrrolidone as a binder, and
    (d) about 7 mg of stearic acid as a lubricant.

90. A method, as set forth in claim 86, wherein the oral sustained release tablet contains
    (a) about 750 mg nicotinic acid,
    (b) about 205 mg hydroxypropyl methylcellulose as a swelling agent,
    (c) about 26 mg polyvinyl pyrrolidone as a binder, and
    (d) about 10 mg stearic acid as a lubricant.

91. A method, as set forth in claim 86, wherein the oral sustained release tablet contains
    (a) about 30% to about 90% by weight nicotinic acid,
    (b) about 5% to about 50% by weight hydroxypropyl methylcellulose as a swelling agent,
    (c) about 1% to about 5% by weight polyvinyl pyrrolidone as a binder, and
    (d) about 0.5% to about 2% by weight stearic acid as a lubricant.

92. A method, as set forth in claim 87, wherein the oral sustained release tablet contains
    (a) about 30% to about 90% parts by weight nicotinic acid, and
    (b) about 5% to about 50% parts by weight hydroxypropyl methylcellulose as a swelling agent.

93. A method, as set forth in claim 77, wherein said single dose treatment during the evening or at night elevates HDL cholesterol in the patient.

94. A method, as set forth in claim 77, wherein said single dose treatment during the evening or at night results in little or no serious increase in a liver function test in the patient, wherein the liver function test is selected from the group consisting of an AST, ALT and alkaline phosphatase liver function test.

95. A method, as set forth in claim 77, wherein said single dose treatment during the evening or at night results in little or no serious increase in uric acid in the patient.

96. A method, as set forth in claim 77, wherein said single dose treatment during the evening or at night results in little or no serious increase in free fasting glucose in the patient.

97. A method of treating hyperlipidemia in a patient comprising orally dosing the patient with an effective amount of nicotinic acid once per day during the evening or at night as a single dose for lowering serum lipids, wherein said single nicotinic acid dosing is accomplished by ingestion of an oral sustained release tablet comprising nicotinic acid, a swelling agent, a binder and a lubricant, wherein said single nicotinic acid dosing during the evening or at night is at least as effective in lowering at least one serum lipid in a patient, wherein the serum lipid is selected from the group consisting of total cholesterol, LDL cholesterol, triglycerides and Lp(a), as treatment with an oral sustained release nicotinic acid preparation when it is dosed in two daily divided doses at a total daily nicotinic acid dosage which is at least equivalent to said single nicotinic acid dose treatment administered during the evening or at night, and wherein said single nicotinic acid dosing administered during the evening or at night causes less elevations in liver function tests than treatment with the oral sustained release nicotinic acid preparation when it is dosed in two daily divided doses at a total daily nicotinic acid dosage which is at least equivalent to said single nicotinic acid dosing administered during the evening or at night.

98. A method, as set forth in claim 97, wherein the patient is dosed with from 250 mg to about 3000 mg of nicotinic acid.

99. A method, as set forth in claim 97, wherein the release rate of said nicotinic acid is from about 2.0% per hour to about 25% per hour.

100. A method, as set forth in claim 97, wherein said single dose treatment during the evening or at night elevates HDL cholesterol in the patient.

101. A method, as set forth in claim 97, wherein said single dose treatment during the evening or at night results in little or no serious increase in a liver function test in a patient wherein the liver function test is selected from the group consisting of an AST, ALT and alkaline phosphatase liver function test.

102. A method, as set forth in claim 97, wherein said single dose treatment during the evening or at night results in little or no serious increase in uric acid in the patient.

103. A method, as set forth in claim 97, wherein said single dose treatment during the evening or at night results in little or no serious increase in free fasting glucose in the patient.

104. A method, as set forth in claim 97, wherein the oral sustained release tablet contains about 5 to about 50 parts by weight of hydroxypropyl methylcellulose per 100 parts by weight of the oral sustained release tablet as the swelling agent.

105. A method, as set forth in claim 97, wherein the oral sustained release tablet further contains about 1 to about 4 parts by weight of a binder per 100 parts by weight of the oral sustained release tablet.

106. A method, as set forth in claim 105, wherein the binder is polyvinyl pyrrolidone.

107. A method, as set forth in claim 97, wherein the oral sustained release tablet further contains about 0.5 to about 2.5 parts by weight of a lubricant per 100 parts by weight of the oral sustained release tablet.

108. A method, as set forth in claim 107, wherein the lubricant is selected from the group consisting of stearic acid and magnesium stearate.

109. A method, as set forth in claim 97, wherein the oral sustained release tablet contains from about 250 mg to about 3000 mg of nicotinic acid.

110. A method, as set forth in claim 97, wherein the sustained release tablet contains
   (a) about 30% to about 90% parts by weight nicotinic acid,
   (b) about 5% to about 50% parts by weight hydroxypropyl methylcellulose as the swelling agent.

111. A method, as set forth in claim 97, wherein the oral sustained release tablet contains
   (a) about 30% to about 90% by weight nicotinic acid,
   (b) about 5% to about 50% by weight hydroxypropyl methylcellulose as a swelling agent,
   (c) about 1% to about 5% by weight a polymer having repeating polymerization unit 1-ethenyl-2-pyrrolidone as a binder, and
   (d) about 0.5% to about 2% by weight stearic acid as a lubricant.

112. A method, as set forth in claim 97, wherein the sustained release tablet contains
   (a) about 375 mg nicotinic acid,
   (b) about 189 mg hydroxypropyl methylcellulose as a swelling agent,
   (c) about 13 mg polyvinyl pyrrolidone as a binder, and
   (d) about 6 mg of stearic acid as a lubricant.

113. A method, as set forth in claim 97, wherein the sustained release tablet contains
   (a) about 500 mg nicotinic acid,
   (b) about 203 mg hydroxypropyl methylcellulose as a swelling agent,
   (c) about 17 mg polyvinyl pyrrolidone as a binder, and
   (d) about 7 mg of stearic acid as a lubricant.

114. A method, as set forth in claim 98, wherein the sustained release tablet contains
   (a) about 750 mg nicotinic acid,
   (b) about 205 mg hydroxypropyl methylcellulose as a swelling agent,
   (c) about 26 mg polyvinyl pyrrolidone as a binder, and
   (d) about 10 mg stearic acid as a lubricant.

115. A method of treating hyperlipidemia in a patient without inducing treatment-limiting (i) hepatotoxicity and (ii) abnormalities in uric acid levels or glucose levels or both, said method comprising orally dosing the patient with an effective antihyperlipidemic amount of nicotinic acid once per day during the evening or at night as a single dose, wherein the nicotinic acid is combined with at least one pharmaceutically acceptable component to form an oral sustained release solid dosage form, wherein the oral sustained release solid dosage form is effective in reducing a serum lipid without causing treatment-limiting (i) hepatotoxicity and (ii) elevations in uric acid levels or glucose levels or both in the patient to a level which would require said treatment to be discontinued by the patient when it is ingested by the patient once per day during the evening or at night as the single dose in accordance with said single dose treatment.

116. A daily method of treating hyperlipidemia in a patient comprising orally administered to the patient a sustained release composition of nicotinic acid once per day during the evening or or night for providing an effective antihyperlipidemic amount of nicotinic acid to the patient to induce at least some lowering of total cholesterol, LDL cholesterol, triglycerides and Lp(a) and at least some increase in HDL cholesterol in the patient's blood stream, without causing abnormalities in liver function tests and uric acid levels or glucose levels to an extent which would require said daily treatment to be discontinued by the patient, the sustained release composition comprising an effective antihyperlipidemic amount of nicotinic acid and an excipient to provide sustained release of the nicotinic acid.

117. A method of claim 116, wherein the effective antihyperlipidemic amount of nicotinic acid is from about 250 mg to about 3000 mg of nicotinic acid.

118. A method of claim 116, wherein the excipient is selected from the group consisting of a swelling agent, a binder, a processing aid and mixtures thereof.

119. A method of claim 118, wherein the swelling agent is selected from group consisting of a polymer, a wax, a natural material and mixtures thereof.

120. A method of claim 119, wherein the polymer is selected from the group consisting of hydroxypropyl methylcellulose, sodium carboxymethylcellulose and ethylcellulose.

121. A method of claim 119, wherein the wax is bees wax.

122. A method of claim 119, wherein the natural material is selected from the group consisting of gums and gelatins.

123. A method of claim 118, wherein the binder is povidone.

124. A method of claim 118, wherein the processing aid is a lubricant.

125. A method of claim 124, wherein the lubricant is stearic acid.

126. A method of claim 120, wherein the hydroxypropyl methylcellulose is in an amount ranging from about 5% to about 50% parts by weight per 100 parts by weight of the sustained release composition.

127. A method of claim 118, wherein the binder is in an amount ranging from about 1% to about 5% parts by weight per 100 parts by weight of the sustained release composition.

128. A method of claim 118, wherein the processing aid is in an amount ranging from about 0.5% to about 2% parts by weight per 100 parts by weight of the sustained release composition.

129. A method of claim 117, wherein the sustained release composition consists essentially of nicotinic acid, hydroxypropyl methylcellulose, povidone and stearic acid.

130. A method of claim 117, wherein the sustained release composition consists essentially of nicotinic acid 375.0 mg, hydroxypropyl methylcellulose 188.7 mg, povidone 12.9 mg., and stearic acid 5.8 mg.

131. A method of claim 116, wherein the sustained release composition consists essentially of nicotinic acid 500.0 mg, hydroxypropyl methylcellulose 203.0 mg, povidone 17.2 mg, and stearic acid 7.3 mg.

132. A method of claim 116, wherein the sustained release composition consists essentially of nicotinic acid 750.0 mg.

hydroxypropyl methylcellulose 204.7 mg.

povidone 25.9 mg. and stearic acid 9.9 mg.

133. A sustained release composition of nicotinic acid for oral administration to a patient once per day during the evening or night for providing an effective antihyperlipidemic amount of nicotinic acid to the patient to induce at least some lowering of total cholesterol, LDL cholesterol, triglycerides and Lp(a) and at least some increase in HDL cholesterol in the patient's blood stream, without causing abnormalities in liver function tests and uric acid levels or glucose levels or both to an extent which would require the use of said sustained release composition by the patient to be discontinued, the sustained release composition comprising (a) an effective antihyperlipidemic amount of nicotinic acid, and (b) an excipient to provide sustained release of the nicotinic acid.

134. A sustained release composition of claim 133, wherein said excipient is selected from the group consisting of a swelling agent, a binder, a processing aid and mixtures thereof.

135. A sustained release composition of claim 134, wherein the swelling agent is selected from group consisting of a polymer, a wax, a natural material and mixtures thereof.

136. A sustained release composition of claim 135, wherein the polymer is selected from the group consisting of hydroxypropyl methylcellulose, sodium carboxymethylcellulose and ethylcellulose.

137. A sustained release composition of claim 135, wherein the wax is bees wax.

138. A sustained release composition of claim 135, wherein the natural material is selected from the group consisting of gums and gelatins.

139. A sustained release composition of claim 134, wherein the binder is povidone.

140. A sustained release composition of claim 134, wherein the processing aid is a lubricant.

141. A sustained release composition of claim 140, wherein the lubricant is stearic acid.

142. A sustained release composition of claim 136, wherein the hydroxypropyl methylcellulose is in an amount ranging from about 5% to about 50% parts by weight per 100 parts by weight of the sustained release composition.

143. A sustained release composition of claim 134, wherein the binder is in an amount ranging from about 1% to about 5% parts by weight per 100 parts by weight of the sustained release composition.

144. A sustained release composition of claim 134, wherein the processing aid is in an amount ranging from about 0.5% to about 2% parts by weight per 100 parts by weight of the sustained release composition.

145. A sustained release composition of claim 133, wherein the sustained release composition consists essentially of nicotinic acid, hydroxypropyl methylcellulose, povidone and stearic acid.

146. A sustained release composition of claim 133, wherein the sustained release composition consists essentially of nicotinic acid 375.0 mg.

hydroxypropyl methylcellulose 188.7 mg.

povidone 12.9 mg. and stearic acid 5.8 mg.

147. A sustained release composition of claim 133, wherein the sustained release composition consists essentially of nicotinic acid 500.0 mg.

hydroxypropyl methylcellulose 203.0 mg.

povidone 17.2 mg. and stearic acid 7.3 mg.

148. A sustained release composition of claim 134, wherein the sustained release composition consists essentially of nicotinic acid 750.0 mg.

hydroxypropyl methylcellulose 204.7 mg.

povidone 25.9 mg. and stearic acid 9.9 mg.

* * * * *

UNITED STATES PATENT AND TRADEMARK OFFICE
CERTIFICATE OF CORRECTION

| | | |
|---|---|---|
| PATENT NO. | : 6,129,930 | |
| APPLICATION NO. | : 08/814974 | |
| DATED | : October 10, 2000 | |
| INVENTOR(S) | : David J. Bova | |

It is certified that error appears in the above-identified patent and that said Letters Patent is hereby corrected as shown below:

On the cover page, under [63], Related U.S. Application Data, change "Continuation-in-part of application No. 08/368,378, Jan. 14, 1995, which is a continuation-in-part of application No. 08/124,392, Sep. 20, 1993, abandoned" to --Continuation-in-part of application No. 08/368,378, Jan. 4, 1995, which is a continuation-in-part of application No. 08/124,392, Sep. 20, 1993, abandoned--

Signed and Sealed this
Twenty-eighth Day of August, 2012

David J. Kappos
*Director of the United States Patent and Trademark Office*